United States Patent
Andersen et al.

(10) Patent No.: US 10,781,245 B2
(45) Date of Patent: *Sep. 22, 2020

(54) ALBUMIN VARIANTS AND USES THEREOF

(71) Applicant: University of Oslo, Oslo (NO)

(72) Inventors: Jan Terje Andersen, Oslo (NO); Inger Sandlie, Oslo (NO); Malin Bern, Oslo (NO)

(73) Assignee: University of Oslo, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 16/250,657

(22) Filed: Jan. 17, 2019

(65) Prior Publication Data

US 2019/0135895 A1     May 9, 2019

Related U.S. Application Data

(63) Continuation of application No. 15/033,503, filed as application No. PCT/IB2014/003002 on Oct. 31, 2014, now Pat. No. 10,208,102.

(60) Provisional application No. 61/936,442, filed on Feb. 6, 2014, provisional application No. 61/898,523, filed on Nov. 1, 2013.

(51) Int. Cl.
*C07K 14/765* (2006.01)
*A61K 38/38* (2006.01)
*A61K 47/64* (2017.01)
*A61K 39/385* (2006.01)
*A61K 39/00* (2006.01)

(52) U.S. Cl.
CPC .......... *C07K 14/765* (2013.01); *A61K 38/385* (2013.01); *A61K 39/385* (2013.01); *A61K 47/643* (2017.08); *A61K 2039/541* (2013.01); *A61K 2039/543* (2013.01); *A61K 2039/6081* (2013.01); *C07K 2319/40* (2013.01)

(58) Field of Classification Search
None
See application file for complete search history.

(56) References Cited

U.S. PATENT DOCUMENTS

| | | |
|---|---|---|
| 2013/0028930 A1 | 1/2013 | Plumridge |
| 2014/0315816 A1 | 10/2014 | Andersen |

FOREIGN PATENT DOCUMENTS

| | | |
|---|---|---|
| WO | 2011/051489 | 5/2011 |
| WO | 2011/124718 | 10/2011 |
| WO | 2012/112188 | 8/2012 |
| WO | 2013/075066 | 5/2013 |
| WO | 2013/135896 | 9/2013 |

OTHER PUBLICATIONS

Andersen et al., "Single-chain variable fragment albumin fusions bind the neonatal Fc receptor (FcRn) in a species-dependent manner: implications for in vivo half-life evaluation of albumin fusion therapeutics." J Biol Chem. Aug. 16, 2013;288(33):24277-85.

Andersen et al., "Extending serum half-life of albumin by engineering neonatal Fc receptor (FcRn) binding." J Biol Chem. May 9, 2014;289(19):13492-502.

Andersen J.T. et al. "Structure-based mutagenesis reveals the albumin-binding site of the neonatal Fc receptor" Nature Communications, vol. 3, Jan. 3, 2012, p. 610.

Chaudhury et al. "Albumin binding to FcRn: distinct from the FcRn-IgG interaction." Biochemistry. Apr. 18, 2006;45(15):4983-90.

Dickinson et al., "Bidirectional FcRn-dependent IgG transport in a polarized human intestinal epithelial cell line." J Clin Invest. Oct. 1999;104(7):903-11.

International Search Report, International Patent Application No. PCT/IB2014/003002, dated Aug. 12, 2015.

Jerdeva et al., "Comparison of FcRn- and pIgR-mediated transport in MDCK cells by fluorescence confocal microscopy." Traffic. Sep. 2010;11(9):1205-20.

Oganesyan et al., "Structural insights into neonatal Fc receptor-based recycling mechanisms." J Biol Chem. Mar. 14, 2014;289(11):7812-24.

Schmidt et al., "Crystal structure of an HSA/FcRn complex reveals recycling by competitive mimicry of HSA ligands at a pH-dependent hydrophobic interface." Structure. Nov. 5, 2013;21(11):1966-78.

Spiekermann et al., "Correction" J Exp Med. Jun. 2, 2003;197(11):1601.

Spiekermann et al., "Receptor-mediated Immunoglobulin G Transport Across Mucosal Barriers in Adult Life" J Exp Med. Aug. 5, 2002;196(3):303-10.

Tesar et al., "Ligand valency affects transcytosis, recycling and intracellular trafficking mediated by the neonatal Fc receptor." Traffic. Sep. 2006;7(9):1127-42.

Yoshida et al., "Human neonatal Fc receptor mediates transport of IgG into luminal secretions for delivery of antigens to mucosal dendritic cells." Immunity. Jun. 2004;20(6):769-83.

Zhu et al., "Calnexin and ERp57 facilitate the assembly of the neonatal Fc receptor for IgG with beta 2-microglobulin in the endoplasmic reticulum." J Immunol. Jul. 15, 2005;175(2):967-76.

Zhu et al., "MHC class I-related neonatal Fc receptor for IgG is functionally expressed in monocytes, intestinal macrophages, and dendritic cells." J Immunol. Mar. 1, 2001;166(5):3266-76.

*Primary Examiner* — Anand U Desai
(74) *Attorney, Agent, or Firm* — Casimir Jones S.C.; J. Mitchell Jones

(57) ABSTRACT

The present invention relates to albumin variants with an improved affinity for the neonatal Fc receptor (FcRn) and uses thereof, and in particular to the use of such albumin variants as carriers for immunogens. In some embodiments, the present invention relates to vaccines (e.g., vaccines for mucosal delivery) comprising albumin/immunogen fusion proteins.

8 Claims, 13 Drawing Sheets
Specification includes a Sequence Listing.

FIG. 1

```
  1 dahksevahr fkdlgeenfk alvliafaqy lqqcpfedhv klvnevtefa ktcvadesae
 61 ncdkslhtlf gdklctvatl retygemadc cakqeperne cflqhkddnp nlprlvrpev
121 dvmctafhdn eetflkkyly eiarrhpyfy apellffakr ykaafteccq aadkaacllp
181 kldelrdegk assakqrlkc aslqkfgera fkawavarls qrfpkaefae vsklvtdltk
241 vhtecchgdl lecaddradl akyicenqds isskIkecce kpllekshci aevendempa
301 dlpsiaadfv eskdvcknya eakdvflgmf lyeyarrhpd ysvvlllrla ktyettlekc
361 caaadphecy akvfdefkpl veepqnlikq ncelfeqlge ykfqnallvr ytkkvpqvst
421 ptlvevsrnl gkvgskcckh peakrmpcae dylsvvlnql cvlhektpvs drvtkcctes
481 lvnrrpcfsa levdetyvpk efnaetftfh adictlseke rqikkqtalv elvkhkpkat
541 keqlkavmdd faafvekcck addketcfae egkklvaasq aalgl
```

FIG. 7A
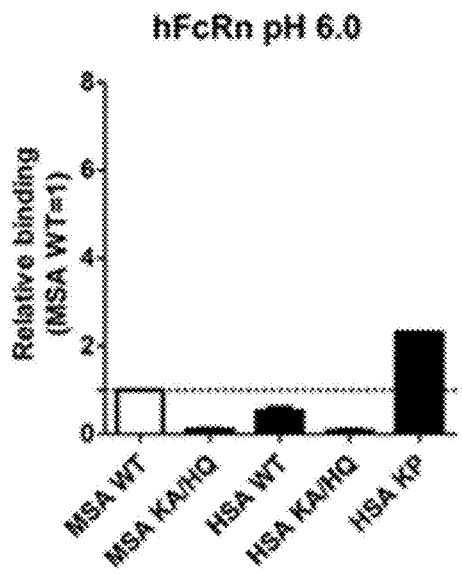
FIG. 7B
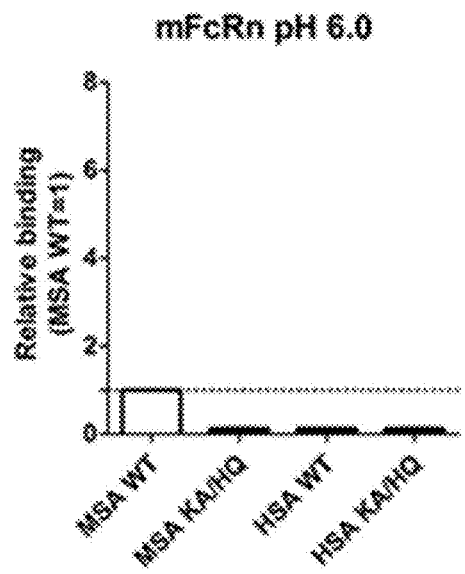
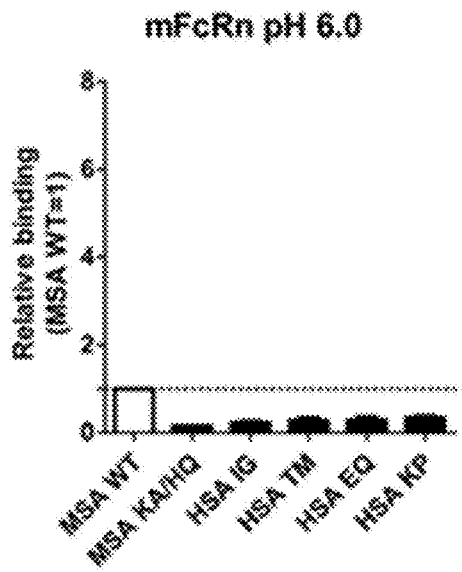
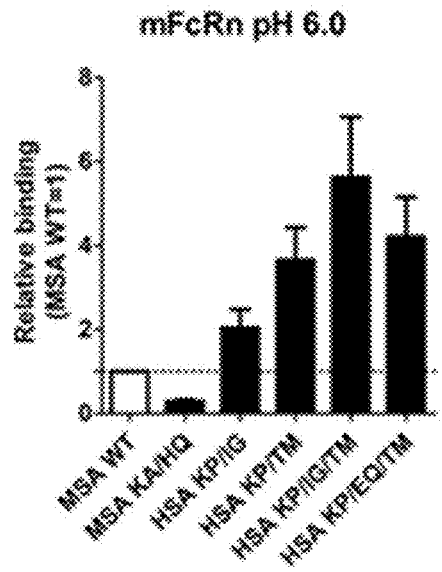

FIG. 8A
FIG. 8B
FIG. 8C
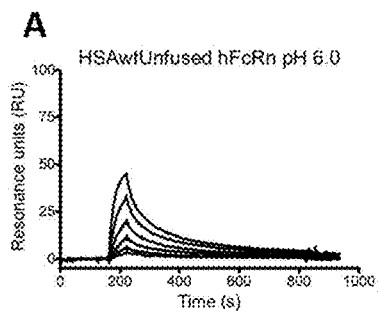
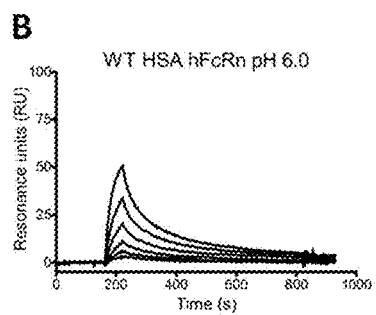
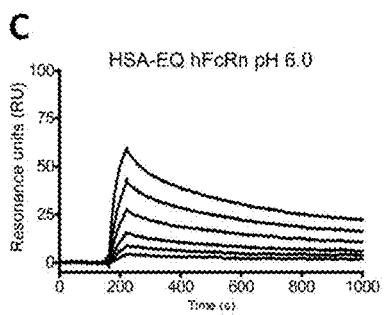
FIG. 8D
FIG. 8E
FIG. 8F
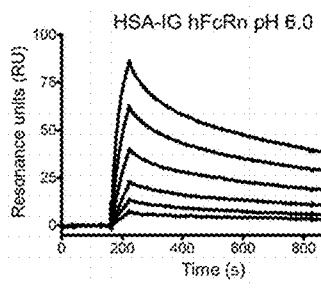
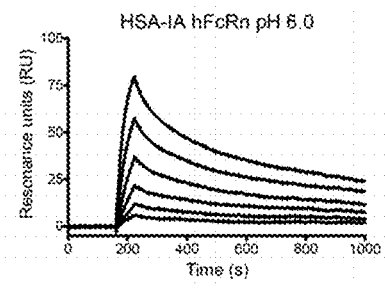
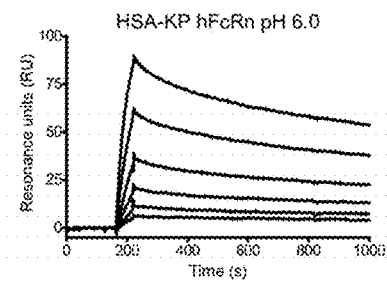
FIG. 8G
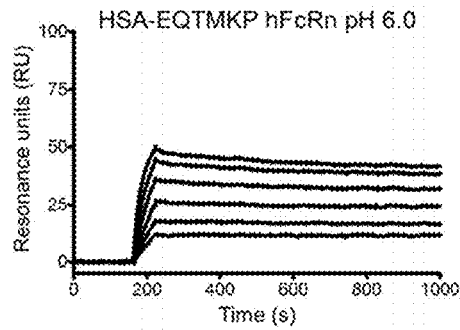

ALBUMIN VARIANTS AND USES THEREOF

CROSS-REFERENCE TO RELATED APPLICATIONS

The present application is continuation of U.S. patent application Ser. No. 15/033,503, filed Apr. 29, 2016, which is a U.S. 371 national phase entry of International Patent Application No. PCT/IB2014/003002, filed Oct. 31, 2014, which claims priority to U.S. Provisional Patent Application No. 61/936,442, filed Feb. 6, 2014 and U.S. Provisional Patent Application No. 61/898,523, filed Nov. 1, 2013, the disclosures of which are herein incorporated by reference in their entireties.

FIELD OF THE INVENTION

The present invention relates to albumin variants with an improved affinity for the neonatal Fc receptor (FcRn) and uses thereof, and in particular to the use of such albumin variants as carriers for immunogens. In some embodiments, the present invention relates to vaccines (e.g., vaccines for mucosal delivery) comprising albumin/immunogen fusion proteins.

BACKGROUND OF THE INVENTION

Albumin is a protein naturally found in the blood plasma of mammals where it is the most abundant protein. It has important roles in maintaining the desired osmotic pressure of the blood and also in transport of various substances in the blood stream. Albumins have been characterized from many species including human beings, pig, mouse, rat, rabbit and goat and it has been found that albumins from different sources share a high degree of structural relationship.

Albumin binds in vivo to the neonatal Fc receptor (FcRn) and this interaction is known to be important for the plasma half-life of albumin (Chaudhury et al 2003; Montoyo et al., 2009). FcRn is a membrane bound protein, and has been found to salvage albumin as well as IgG from intracellular degradation (Roopenian D. C. and Akilesh, S. (2007), Nat. Rev. Immunol 7, 715-725.). Thus, FcRn is a bifunctional molecule that contributes to the maintaining the high level of IgG and albumin in serum of mammals such as humans.

While the FcRn-IgG interaction has been characterized in the prior art, the FcRn-albumin is less well characterized. Data indicated that IgG and albumin bind noncooperatively to distinct sites on FcRn (Andersen et al. (2006), Eur. J. Immunol 36, 3044-3051; Chaudhury et al. (2006), Biochemistry 45, 4983-4990). It is known that mouse FcRn binds IgG from mice and humans whereas human FcRn appears to be more discriminating (Ober et al. (2001) Int Immunol 13, 1551-1559) and does not bind mouse IfG (Ober et al. (2001) Int Immunol 13, 1551-1559). Furthermore, human FcRn binds albumin from both mouse and human, whereas mouse FcRn does not bind human albumin (Andersen et al (2010) JBC).

Human serum albumin (HSA) has been well characterized as a polypeptide of 585 amino acids, the sequence of which can be found in Peters, T., Jr. (1996) All about Albumin: Biochemistry, Genetics and Medical, Applications, Academic Press, Inc., Orlando. It has a characteristic binding to its receptor FcRn, where it binds at pH 6.0 but not at pH 7.4. The serum half-life of HSA has been found to be approximately 19 days. A natural variant having lower plasma half-life has been identified (Biochim Biophys Acta. 1991, 1097:49-54) having the substitution D494N. This substitution generated an N-glycosylation site in this variant, which is not present in the wild type HSA. It is not known whether the glycosylation or the amino acid change is responsible for the change in plasma half-life.

Albumin has a long serum half-life and because of this property it has been used for drug delivery. Albumin has been conjugated to pharmaceutically beneficial compounds (WO0069902A), and it was found that conjugate had maintained the long plasma half-life of albumin so the resulting plasma half-life of the conjugate has generally been found to be considerably longer than the plasma half-life of the beneficial therapeutic compound alone.

Further, albumin has been fused to therapeutically beneficial peptides (WO 01/79271 A and WO 03/59934 A) with the typical result that the fusion has the activity of the therapeutically beneficial peptide and a long plasma half-life considerably longer than the plasma half-life of the therapeutically beneficial peptides alone.

Albumin has the ability to bind a number of ligands, and this property has been utilized to extend the plasma half-life of drugs having the ability to bind to albumin. This has been achieved by binding a pharmaceutical beneficial compound to a moiety having albumin binding properties. It is not clear what determines the plasma half-life of the formed conjugates or fusion polypeptides but it appears to be given by the albumin and the selected pharmaceutically beneficial compound/peptide they are composed of. It would be desirable to be able to control the plasma half-life of a given albumin conjugate or albumin fusion polypeptide so that a longer or shorter plasma half-life than given by the components of the conjugate/fusion can be achieved, in order to be able to design a particular drug or vaccine according to the particulars of the indication intended to be treated.

SUMMARY OF THE INVENTION

The present invention relates to albumin variants with an improved affinity for the neonatal Fc receptor (FcRn) and uses thereof, and in particular to the use of such albumin variants as carriers for immunogens and as therapeutics. In some embodiments, the present invention relates to vaccines (e.g., vaccines for mucosal delivery) comprising albumin/immunogen fusion proteins.

In some embodiments, the present invention provides a variant human serum albumin (HSA) or mouse serum albumin (MSA) that binds to FcRn with increased affinity relative to wild type HSA or MSA, wherein the polypeptide comprises at least one variant amino acid. In some embodiments, the polypeptide binds to FcRn with a Kd of 10 or less, 5 or less, or 1 or less (e.g., measured under acid conditions). In some embodiments, the polypeptide is transported across polarized human cells at a higher level than wild-type albumin (e.g. as measured in ng/ml after 4 hours in a polarized human cell assay). In some embodiments, the higher level is at least 2, 3, 4, 5, or 10-fold higher than wild type albumin. In some embodiments, the efficiency is more than 10 ng/ml (e.g. more than 15 ng/ml, or more than 30 ng/ml).

In some embodiments, the variant polypeptide is at least 80%, 90%, or 95% identical to SEQ ID NO:1 or wild type MSA. In some embodiments, the variant amino acid is, for example, one or more of K573Y, I523G, I253A, T527M, E505Q, K573P, K573Y/I523G, K573Y/I523G/T527M, K573Y/E505Q/T527M, K573Y/T527M, K573P/I523G, K573P/I523G/T527M, K573P/E505Q/T527M, K573P/T527M, V547A, V547A/K573P, V547A/E505Q/K573P/

T527M or K500A/H510Q of SEQ ID NO:1, deletion of domain III of HSA, or K500A/H510Q of wild type MSA.

In some embodiments, the present invention provides an albumin variant, fragment thereof, or fusion thereof comprising a mutation (e.g., substitution mutation in a position corresponding to one or more of positions 573, 523, 527, 505, or domain III of SEQ ID NO:1 or a variant of MSA, wherein said albumin has increased or decreased binding to hFcRn or mFcRn compared to wildtype albumin. In some embodiments, the present invention provide a fusion protein of the albumin variant; and an immunogen (e.g., antigen) conjugated to an amino acid of the albumin. In some embodiments, the altered binding to FcRn as compared to wildtype albumin is an increased binding affinity. In some embodiments, the albumin variant is K573Y, I523G, I253A, T527M, E505Q, K573P, K573Y/I523G, K573Y/I523G/T527M, K573Y/E505Q/T527M, K573Y/T527M, K573P/I523G, K573P/I523G/T527M, K573P/E505Q/T527M, K573P/T527M, K500A/H510Q, V547A, V547A/K573P, V547A/E505Q/K573P/T527M, or a domain III deletion of SEQ ID NO:1. In some embodiments, the albumin variant is a K500A/H510Q of MSA. In some embodiments, the immunogen is covalently attached to an amino acid comprising a thiol group.

In some embodiments, the present invention provides a nucleic acid encoding the albumin variant, fragment thereof, or fusion thereof-immunogen fusion protein as described above. In some embodiments, the present invention provides host cells comprising the nucleic acids.

In some embodiments, the present invention provides a composition (e.g., vaccine composition) comprising the albumin variant or fusion protein described above and a pharmaceutically acceptable carrier. In some embodiments, the composition is formulated as a vaccine for mucosal administration.

In some embodiments, the present invention provides a method of inducing an immune response (e.g., mucosal immune response) in a subject comprising administering to the subject an fusion protein comprising an albumin variant, fragment thereof, or fusion thereof; and an immunogen as described above. In some embodiments, the present invention provides for the use of the fusion protein comprising albumin variant, fragment thereof, fusion thereof or conjugate thereof; and an immunogen as described above to treat a subject.

Further embodiments provide a vaccine composition comprising: a) a fusion protein comprising a wild type albumin polypeptide and a conjugate (e.g. an immunogen); and b) a pharmaceutically acceptable carrier. Additional embodiments provide methods and uses of inducing an immune response in a subject, comprising administering to the subject the aforementioned vaccine composition under conditions such that said subject generates an immune response to the immunogen. In some embodiments, the vaccine composition is aerosolized. In some embodiments, the vaccine composition is delivered to a mucosal surface of the subject (e.g., instranasally).

Additional embodiments are described herein.

BRIEF DESCRIPTION OF THE DRAWINGS

FIG. 1 provides SEQ ID NO:1, wildtype HSA.

FIG. 2A and FIG. 2B shows a crystallographic illustration of the HSA positions targeted by mutagenesis.

FIG. 3 shows a cassette vector system for production of albumin fusions.

FIG. 4A and FIG. 4B shows SDS-PAGE analysis of purified albumin-GST variants. Representative non-reducing SDS-PAGE gel analyses of (A) HSA-GST variants and B (MSA-GST variants).

FIG. 5A-E shows binding of HSA-GST variants to hFcRn. (A-D) ELISA measurements. showing binding of WT HSA-GST and mutant variants to hFcRn at pH 6.0. (E) Relative binding of HSA-GST variants to hFcRn at pH 6.0. Relative binding was calculated based on the ELISA results (A-D), where WT FcRn binding was set to 1. The results are representative for at least three independent experiments.

FIG. 6A-D shows binding of MSA and HSA-GST variants to hFcRn and mFcRn. ELISA measurements showing binding of WT HSA and MSA-GST fusions as well as mutant variants to (A) hFcRn and (B-D) mFcRn at pH 6.0. Relative binding of WT HSA and MSA-GST fusions as well as mutant variants to hFcRn at pH 6.0. Relative binding of WT HSA and MSA-GST fusions as well as mutant variants to mFcRn at pH 6.0. Relative binding was calculated based on the ELISA results where WT was set to 1. The results are representative for at least three independent experiments.

FIG. 7A-B shows relative binding of MSA and HSA-GST variants to hFcRn and mFcRn (A) Relative binding of MSA and HSA-GST variants to (A) hFcRn and (B-D) mFcRn at pH 6.0. Relative binding was calculated based on the ELISA results in FIG. 6, where WT FcRn binding was set to 1. The results are representative for at least three independent experiments.

FIG. 8A-G shows SPR binding of monomeric hFcRn to immobilized HSA variants. Binding of titrated amounts of monomeric hFcRn injected over immobilized (A) unfused WT HSA (B) WT HSA-GST, (C), HSA-EQ-GST (D), HSA-IG-GST (E) HSA-IA-GST, (F) HSA-KP-GST and (G) HSA-EQ/TM/KP. The binding data were fitted to a 1:1 Langmuir binding model supplied with the BIAevaluation software. The estimated binding kinetics are summarized in Table 2.

FIG. 9 shows FcRn-mediated transcytosis of engineered HSA fusion variants across a polarized human epithelial cell layer. ELISA quantification of the amounts of WT HSA, KA/HQ HSA and KP HSA fusions transported from the apical to the basolateral side of polarized T84 cells grown in a Transwell system. Samples were collected at time point's 0 h and 4h from the basolateral reservoirs, and the amounts transcytosed are expressed as ng/ml HSA fusion transcytosed. The results represent the mean of four independent experiments.

FIG. 10A-C shows SPR binding of monomeric hFcRn to immobilized HSA variants. Binding of titrated amounts of monomeric hFcRn injected over immobilized (A) V547A (1 μM-0.031 μM) (B) V547A/K573P (1 μM-0.031 μM) and (C) E505Q/T527MN547A/K573P (0.25 μM-3.9 μM).

FIG. 11A-F shows ELISA binding of HSA-GST variants to hFcRn at pH 7.4.

FIG. 12A and FIG. 12B shows ELISA binding of HSA-GST variants to hFcRn. ELISA measurements showing binding of WT HSA-GST and mutant variants to hFcRn at pH 6.0. (B) ELISA measurements showing binding of WT HSA-GST and mutant variants to hFcRn at pH 7.4.

FIG. 13 shows transcytosis of non-fused HSA variants across polarized human cells. ELISA quantification of the amounts of non-fused WT HSA and KP transported from the apical (A) to the basolateral (B) side and from B to A side of polarized T84 cells grown in a Transwell system.

FIG. 14 shows transcytosis of HSA-GST variants across polarized human cells. ELISA quantification of the amounts of HSA WT, EQ, TM and KP/EQ/TM GST fusions transported from the apical to the basolateral side of polarized T84 cells grown in a Transwell system.

DEFINITIONS

Figure 2A:
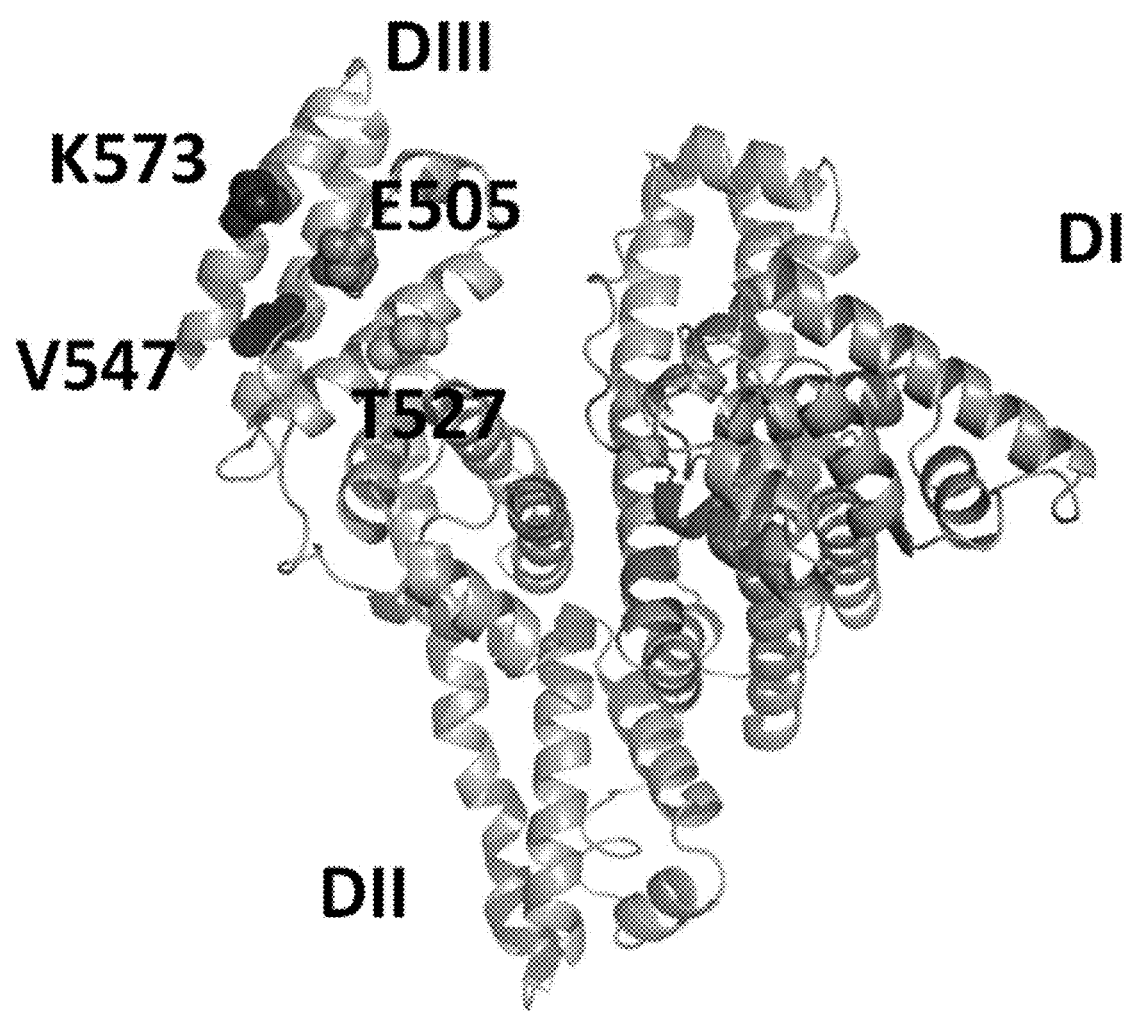

The term "albumin" as used herein means a protein having substantially the same three dimensional structure as HSA. Examples of albumin proteins according to the invention include, but are not limited to, human serum albumin, primate serum albumin, such as chimpanzee serum albumin, gorilla serum albumin, rodent serum albumin such as rabbit serum albumin, mouse albumin and rat serum albumin, bovine serum albumin, equine serum albumin, donkey serum albumin, hamster serum albumin, goat serum albumin, sheep serum albumin, dog serum albumin, guinea pig serum albumin, chicken serum albumin and pig serum albumin. HSA as disclosed in SEQ ID NO: 1 or any naturally occurring allele thereof, is the preferred albumin according to the invention and has a molecular weight of 67 kDa. The skilled person will appreciate that natural alleles may exist having essentially the same properties as HSA but having one or a few changes compared to SEQ ID NO: 1, and the inventors also contemplate the use of such natural alleles.

The term "fragments of albumin" as used herein means a part of albumin having retained the ability to bind to FcRn. Fragments may consist of one uninterrupted sequence derived from HSA or is may comprise two or more sequences derived from HSA. The fragments according to the invention have a size of more than approximately 20 amino acid residues, preferably more than 30 amino acid residues, more preferred more than 40 amino acid residues, more preferred more than 50 amino acid residues, more preferred more than 75 amino acid residues, more preferred more than 100 amino acid residues, more preferred more than 200 amino acid residues, more preferred more than 300 amino acid residues, even more preferred more than 400 amino acid residues and most preferred more than 500 amino acid residues.

The term "wildtype" when used in reference to a protein refers to proteins encoded by the genome of a cell, tissue, or organism, other than one manipulated to produce synthetic proteins.

The term "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitutions refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; unnatural amino acids like p-aminophenylalanine, a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on). For an amino acid substitution, the following nomenclature is used: Original amino acid, position, substituted amino acid. Accordingly, the substitution of lysine with alanine at position 573 is designated as "K573A" and the substitution of lysine with proline at position 573 is designated as K573P. Multiple mutations are separated by addition marks ("+") or "/", e.g., "Gly205Arg+Ser411Phe" or "G205R/S411F", representing mutations at positions 205 and 411 substituting glycine (G) with arginine (R), and serine (S) with phenylalanine (F), respectively.

The relatedness between two amino acid sequences or between two nucleotide sequences is described by the parameter "identity". For purposes of the present invention, the degree of identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends in Genetics 16: 276-277), preferably version 3.0.0 or later. The optional parameters 11644.000-EP7 used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows: (Identical Residues×100)/(Length of Alignment−Total Number of Gaps in Alignment).

The expression "amino acid position corresponding to" a position in a reference sequence and similar expression is intended to identify the amino acid residue that in the primary or spatial structure corresponds to the particular position in the reference sequence. The skilled person will appreciate that this can be done by aligning a given sequence with the reference sequence and identifying the amino acid residue that aligns with the particular position in the reference sequence. For example in order to find the amino acid residue in a given albumin sequence that corresponds to position 573 in HSA, the given albumin sequence is aligned with HSA and the amino acid that aligns with position 573 in HSA is identified as the amino acid in the given albumin sequence that corresponds to position 573 in HSA.

The expression Xnnn is intended to mean an amino acid residue X located in a position corresponding to position nnn in HSA and the expression XnnnY is intended to mean a substitution of any amino acid X located in a position corresponding to position nnn in HSA with the amino acid residue Y.

As used herein, the term "affinity" refers to a measure of the strength of binding between two members of a binding pair, for example, an albumin and FcRn. $K_d$ is the dissociation constant and has units of molarity. The affinity constant is the inverse of the dissociation constant. An affinity constant is sometimes used as a generic term to describe this chemical entity. It is a direct measure of the energy of binding. The natural logarithm of K is linearly related to the Gibbs free energy of binding through the equation $\Delta G_0 = -RT \, LN(K)$ where R=gas constant and temperature is in degrees Kelvin. Affinity may be determined experimentally, for example by surface plasmon resonance (SPR) using commercially available Biacore SPR units (GE Healthcare).

As used herein, the term "conjugate" as in "a fusion protein comprising an albumin and a conjugate" refers to any molecule attached (e.g., covalently as in a fusion protein or non-covalently (e.g., via hydrophobic interactions)) to a albumin. Examples include, but are not limited to, peptides, polypeptides, immunogens, drugs, proteins, lipids, small molecules, nucelotides, radioactive tracers etc.

As used herein, the term "under conditions such that said subject generates an immune response" refers to any qualitative or quantitative induction, generation, and/or stimulation of an immune response (e.g., innate or acquired).

A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T cells (e.g., antigen-specific T cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired (e.g., immune responses that are mediated by B and T cells following a previous exposure to antigen (e.g., that exhibit increased specificity and reactivity to the antigen)).

As used herein, the term "immunogen" refers to an agent (e.g., a microorganism (e.g., bacterium, virus or fungus) and/or portion or component thereof (e.g., a protein antigen)) that is capable of eliciting an immune response in a subject. In some embodiments, immunogens elicit immunity against the immunogen (e.g., microorganism (e.g., pathogen or a pathogen product)).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The present invention relates to albumin variants with an improved affinity for the neonatal Fc receptor (FcRn) and uses thereof, and in particular to the use of such albumin variants as carriers for immunogens. In some embodiments, the present invention relates to vaccines (e.g., vaccines for mucosal delivery) comprising albumin/immunogen fusion proteins.

The principle binding site for FcRn on albumin was first shown to be located within the C-terminal DIII (Andersen et al., Nat Commun. 2012 Jan. 3; 3:610; Chaudhury et al. Biochemistry. 2006 Apr. 18; 45(15):4983-90). Then, targeting of three fully conserved histidine residues within DIII of human albumin (His464, His510 and His535) by site-directed mutagenesis revealed that all are crucial for binding (Andersen et al., 2012, supra). A docking model of the human FcRn-human albumin complex was built, where in addition to DIII, two exposed loops within the N-terminal DI were shown to be in proximity to the receptor (Andersen et al., 2012, supra). In agreement with these predictions, two recently published co-crystal structures of human FcRn in complex with human albumin confirmed the contributions from both DI and DIII (Oganesyan et al., J Biol Chem. 2014 Mar. 14; 289(11):7812-24.; Schmidt et al., Structure. 2013 Nov. 5; 21(11):1966-78). One of the co-crystal structures contains wild-type albumin and the other an engineered human albumin variant (HSA13) with four amino acid substitutions (V418M, T420A, E505G, and V547A). The latter has improved affinity for FcRn at both pH 6 and pH 7.4. The two co-crystal structures show highly similar modes of binding, but with some differences that are likely due to the introduced mutations in HSA13 DIII. Furthermore, both co-crystal structures show the two exposed loops in DI in contact with FcRn.

Several studies have shown that human FcRn can transport both monomeric IgG and IgG-containing immune complexes across mucosal epithelial barriers in both directions (Zhu et al., J Immunol. 2005 Jul. 15; 175(2):967-76; Yoshida et al., Immunity. 2004 June; 20(6):769-83; Spiekermann et al., J Exp Med. 2002 Aug. 5; 196(3):303-10. Erratum in: J Exp Med. 2003 Jun. 2; 197(11):1601; Dickinson et al., J Clin Invest. 1999 October; 104(7):903-11; Zhu et al., J Immunol. 2001 Mar. 1; 166(5):3266-76)).

Using polarized Madin-Darby canine kidney (MDCK) cells that over-express FcRn it was demonstrated that the receptor transports IgG by transcytosis from either the apical or the basolateral side (Zhu et al., J Immunol. 2001 Mar. 1; 166(5):3266-76; Jerdeva et al., Traffic. 2010 September; 11(9):1205-20).

These findings raise the question of whether or not FcRn is capable of mediating transcytosis of albumin, and whether the stoichiometry of the interactions with FcRn plays a role, as albumin binds FcRn in a 1:1 manner, while IgG is homodimeric and has two binding sites for FcRn. So far, one study using MDCK cells indicate that albumin is not transcytosed (Tesar et al., Traffic. 2006 September; 7(9):1127-42).

Yeast display has been used to develop human albumin variants with a range of affinities toward human FcRn. One such variant (E505GN547A) gained more than 10-fold improved affinity at pH 6.0 with a minor increase at neutral pH, which extended the half-life in human FcRn transgenic mice and cynomolgus monkeys by 1.5-fold and 1.3-fold, respectively (Schmidt et al., Structure. 2013 Nov. 5; 21(11): 1966-78).

Furthermore, using an approach based on structural analysis and cross-species binding analyses, a single substituted human albumin variant (K573P) was identified with 12-fold improved affinity towards human FcRn at acidic pH without detectable binding at neutral pH (Andersen et al., J Biol Chem. 2014 May 9; 289(19):13492-502.). When evaluated in mice transgenic for human FcRn and cynomolgus monkeys the engineered variant showed 1.4 and 1.6-fold extended half-life, respectively.

As described above, embodiments of the present invention provide fusion proteins comprising an immunogen and an albumin variant with enhanced or decreased affinity for FcRn relative to wild type albumin. The engineered albumin variants and derived fragments with altered FcRn binding properties have improved immunogenicity, as a consequence of 1) improved transcytosis by FcRn; 2) improved biodistribution/serum half-life as a function of the molecular weight above the renal clearance threshold; 3) increased FcRn mediated rescue from degradation; 4) increased presentation on MHC class I and II due to FcRn mediated enhanced intracellular transport and processing by dendritic cells; 5) suitability for mucosal delivery; and 6) increased thermal stability as albumin is a very stable molecule.

Vaccine subunits fused to such albumin variants do not interfere with FcRn binding. As FcRn functions in rescue from degradation, drives antigen presentation on MHC class I and II and allows for mucosal delivery, the pharmacokinetics and immunogenicity of the vaccines of embodiments of the present invention are improved relative to immunogens not bound to the variant albumin polypeptides. Thus, embodiments of the present invention provide improved vaccine compositions and uses thereof that overcome limitations of existing vaccines.

Experiments conducted during the course of development of embodiments of the present invention generated full length albumins as well as fragments derived thereof with altered FcRn binding properties. Such variants showed retained FcRn binding when fused genetically to a number of peptides and folded protein domains.

Embodiments of the present invention provide vaccines for use in mucosal delivery. The role of FcRn in vaccination and mucosal delivery has been demonstrated and described in the literature for Fc-fusions. Infectious agents such as viruses and bacteria enter the body at mucosal surfaces. Intramuscular or subcutaneous vaccination usually provides only minimal protection at sites of infection owing to suboptimal delivery and activation of the mucosal immune system. There is a close association between mucosal epithelial cells and the immune effector cells within the laminar propria, and delivery of vaccines through the mucosal surface may therefore be an ideal approach. The mucosa is a selective barrier that prevents efficient entry. Embodiments of the present invention provide compositions and methods for circumvent this problem by targeting mucosal vaccines to FcRn expressed at the mucosal epithelium. This provides secure specific transport of the intact subunit vaccines across the epithelial barrier to the mucosal immune system for subsequent induction of immune cell activation and memory.

Vaccines of embodiments of the present invention designed for mucosal delivery utilize the FcRn mediated transcytosis pathway for mucosal delivery of therapeutics or subunit vaccines (antigen/immunogen) based on fusion (chemically or genetically) to full length albumin, or albumin mutants or fragment with altered FcRn binding properties. Such vaccines find use in prevention and treatment of infection (e.g., by microorganisms), as well as in the prevention of virus induced cancers. In other embodiments, the fusions are utilized to deliver therapeutics to specific mucosal body sites. Thus, embodiments of the present invention provide methods and compositions for local delivery to the infected/inflamed site or to the site of cancer.

In some embodiments, the present invention provides human and mouse albumin variants with substitutions at one or more of positions 573, 253, 523, 527, and 505 of HSA or positions 500 or 510 of MSA. In some embodiments, the variation is a deletion. For example, in some embodiments, the variant is K573Y, I523G, I253A, T527M, E505Q, K573P, K573Y/I523G, K573Y/I523G/T527M, K573Y/E505Q/T527M, K573Y/T527M, K573P/I523G, K573P/I523G/T527M, K573P/E505Q/T527M, K573P/T527M, K500A/H510Q, V547A, V547A/K573P, V547A/E505Q/K573P/T527M or a domain III deletion of SEQ ID NO:1. In some embodiments, the albumin variant is a K500A/H510Q of MSA.

The present invention encompasses variants that comprise mutations (e.g., substitutions, deletions or additions) at positions other than positions described, so long as the substitution at the described position is maintained. Accordingly, in some embodiments, the albumin variants are at least 80%, 90%, 95%, 97% or 99% identical to a wildtype serum albumin (e.g., wildtype HSA, SEQ ID NO:1 or wild type MSA), with the proviso that the albumin variant comprises a one of the mutations or deletions described herein. In some embodiments, the present invention provides fragments of the variant albumin. As above, the fragments are preferably at least 80%, 90%, 95%, 97% or 99% identical to a portion of SEQ ID NO:1 (i.e., the parent albumin of the fragment). In some embodiments, the present invention provides fusion proteins comprising heterologous polypeptide sequence fused to a variant albumin or fragment thereof. As above, the variant albumins and fragments that form a portion of the fusion protein are preferably at least 80%, 90%, 95%, 97% or 99% identical to SEQ ID NO:1 or a portion thereof (i.e., the parent albumin of the fragment), and comprise a substitution mutation as described herein.

In some embodiments, the variant albumins, fragments and fusions thereof have an increased affinity for human or mouse FcRn as compared to the corresponding wildtype sequence. The skilled person will understand that any suitable method might be useful to determine whether the affinity of a variant albumin to FcRn is higher or lower than the affinity of the parent albumin to FcRn, e.g. determination and comparison of the binding constants Kd. Thus, according to the invention variant albumins having a Kd that is lower than the Kd for natural HSA is considered to have a higher plasma half-life than HSA and variant albumins having a Kd that is higher than the Kd for natural HSA is consider to have a lower plasma half-life than HSA.

In some embodiments, HSA variants comprise one or more amino acid substitutions. In some embodiments, the amino acid substitutions are at positions 547, 573, 253, 523, 527, and 505 of HSA or positions 500 or 510 of MSA. In some embodiments, the substitutions result in higher affinity for FcRn (e.g., lower Kd). For example, in some embodiments, variants have a Kd of 10, or lower, 5 or lower, or 1 or lower. In some embodiments, substitutions are conservative or non-conservative changes. In some embodiments, one or more variants at a given positions that have similar side chains to the variants described herein are specifically contemplated (e.g., conservative changes relative to the variants described herein).

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Exemplary conservative amino acids substitution groups are: valine-leucine-isoleucine, phenylalanine-tyrosine, lysine-arginine, alanine-valine, and asparagine-glutamine.

Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic hydroxyl; (4) aromatic (phenylalanine, tyrosine, tryptophan); (5) amide (asparagine, glutamine); and (6) sulfur containing (cysteine and methionine) (e.g., Stryer ed., Biochemistry, pg. 17-21, 2nd ed, WH Freeman and Co., 1981).

In some embodiments, a variant includes "nonconservative" changes (e.g., replacement of a glycine with a tryptophan). Guidance in determining which amino acid residues can be substituted, inserted, or deleted without abolishing biological activity can be found using computer programs.

The albumin or fragment thereof according to the invention may be conjugated to an immunogen (e.g., antigen) using techniques known within the art. The present invention is not limited to a particular immunogen. Any immunogen or antigenic fragment may be utilized. Examples include, but are not limited, immunogens derived from microorganisms (e.g., pathogenic microorganisms), tumors (e.g., for cancer vaccines) and the like.

The variant albumins, fragments thereof, and fusions of the present invention can be prepared using techniques well known to the skilled person. One convenient way is by cloning nucleic acid encoding the parent albumin, fragment thereof or fusion polypeptide comprising the substitution mutations described herein.

The fusion proteins comprising variant albumins, fragments thereof, and fusions of the present invention may also be connected to a signal sequence in order to have the polypeptide secreted into the growth medium during culturing of the transformed host organism. It is generally advantageous to have the variant polypeptide secreted into the growth medium in order to ease recovery and purification.

Techniques for preparing variant polypeptides have also been disclosed in WO 2009019314 (included by reference) and these techniques may also be applied to the present invention. Albumins have been successfully expressed as recombinant proteins in a range of hosts including fungi (including but not limited to Aspergillus (WO06066595), Klyveromyces (Fleer 1991, Bio/technology 9, 968-975), Pichia Pichia (Kobayashi 1998 Therapeutic Apheresis 2, 257-262) and Saccharomyces (Sleep 1990, Bio/technology 8, 42-46)), bacteria (Pandjaitab 2000, J. Allergy Clin. Immunol 105, 279-285)), animals (Barash 1993, Transgenic Research 2, 266-276) and plants (including but not limited to potato and tobacco (Sijmons 1990, Bio/technology 8, 217 and Farran 2002, Transgenic Research 11, 337-346). The HSA domain III derivative, fragment, or variant thereof of the invention is preferably produced recombinantly in a suitable host cell. In principle any host cell capable of producing a polypeptide in suitable amounts may be used and it is within the skills of the average practitioner to select a suitable host cell according to the invention. A preferred host organism is yeast, preferably selected among Saccharomycacae, more preferred Saccharomyces cerevisiae.

The fusion proteins comprising variant albumins, fragments thereof, and fusions of the present invention may be recovered and purified from the growth medium using a combination of known separation techniques such as filtrations, centrifugations, chromatography, affinity separation techniques etc. It is within the skills of the average practitioner to purify the variant albumins, fragments thereof, and fusions of the invention using a particular combination of such known separation steps. As an example of purification techniques that may be applied to the variants of the present invention can be mentioned the teaching of WO0044772.

In some embodiments, fusion proteins are expressed from fusion nucleic acids using molecular biology techniques known in the art. The one or more immunogen polypeptides may be fused to the N-terminus, the C-terminus of the albumin variant or fragment thereof, inserted into a loop in the albumin variant or fragment thereof structure or any combination thereof. It may or it may not comprise linker sequences separating the various components of the fusion polypeptide. Teachings relating to fusions of albumin or a fragment thereof are known in the art and the skilled person will appreciate that such teachings can also be applied to the present invention. WO 01/79271 A and WO 03/59934 A also contains examples of polypeptides that may be fused to the albumin variants and fragments thereof of the present invention and these examples apply also for the present invention.

The albumin variants or fragments thereof or fusion polypeptides comprising the albumin variants of fragments thereof according to the invention have the benefit that their plasma half-life is altered compared to the parent albumin variants or fragments thereof or fusion polypeptides comprising the albumin variants of fragments thereof. This has the advantage that the plasma half-life of conjugates comprising albumin variants or fragments thereof or fusion polypeptides comprising the albumin variants of fragments thereof according to the invention can be selected in accordance with the particular therapeutic purpose.

In other embodiments, albumin variants are conjugated to immunogens. Techniques for conjugating immunogens to the albumin derivative, fragment, or variant thereof are known in the art. WO2009019314 discloses examples of techniques suitable for conjugating a therapeutically compound to a polypeptide which techniques can also be applied to the present invention. Further WO2009019314 discloses examples of compounds and moieties that may be conjugated to substituted transferrin and these examples may also be applied to the present invention. The teaching of WO2009019314 is included herein by reference.

HSA contains in its natural form one free thiol group that conveniently may be used for conjugation. As a particular embodiment within this aspect the variant albumins, fragments thereof, and fusions of the present invention may comprise further modifications provided to generate additional free thiol groups on the surface. This has the benefit that the pay load of the albumin derivative, fragment, or variant thereof is increased so that more than one molecule of the immunogen can be conjugated to each albumin derivative, fragment, or variant thereof, or two or more different immunogens may be conjugated to each molecule of the variant albumins, fragments thereof, and fusions. Teaching of particular residues that may be modified to provide for further free thiol groups on the surface can be found in the co-pending patent application (EP 2009 152 625.1), which is incorporated by reference.

In some embodiments, the present invention provides vaccine compositions comprising an albumin variant or wild type albumin described herein and an immunogen. The present invention is not limited by the particular formulation of a composition comprising an albumin/immunogen fusion. Indeed, a vaccine composition of the present invention may comprise one or more different agents in addition to the fusion protein. These agents or cofactors include, but are not limited to, adjuvants, surfactants, additives, buffers, solubilizers, chelators, oils, salts, therapeutic agents, drugs, bioactive agents, antibacterials, and antimicrobial agents (e.g., antibiotics, antivirals, etc.). In some embodiments, a vaccine composition comprising a fusion protein comprises an agent and/or co-factor that enhance the ability of the immunogen to induce an immune response (e.g., an adjuvant). In some preferred embodiments, the presence of one or more co-factors or agents reduces the amount of immunogen required for induction of an immune response (e.g., a protective immune respone (e.g., protective immunization)). In some embodiments, the presence of one or more co-factors or agents can be used to skew the immune response towards a cellular (e.g., T cell mediated) or humoral (e.g., antibody mediated) immune response. The present invention is not limited by the type of co-factor or agent used in a therapeutic agent of the present invention.

Adjuvants are described in general in Vaccine Design—the Subunit and Adjuvant Approach, edited by Powell and Newman, Plenum Press, New York, 1995. The present invention is not limited by the type of adjuvant utilized (e.g., for use in a composition (e.g., pharmaceutical composition). For example, in some embodiments, suitable adjuvants include an aluminium salt such as aluminium hydroxide gel (alum) or aluminium phosphate. In some embodiments, an adjuvant may be a salt of calcium, iron or zinc, or may be an insoluble suspension of acylated tyrosine, or acylated sugars, cationically or anionically derivatised polysaccharides, or polyphosphazenes.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

Although an understanding of the mechanism is not necessary to practice the present invention and the present invention is not limited to any particular mechanism of action, in some embodiments, compositions and methods of the present invention induce expression and secretion of cytokines (e.g., by macrophages, dendritic cells and CD4+ T cells). Modulation of expression of a particular cytokine can occur locally or systemically. It is known that cytokine profiles can determine T cell regulatory and effector functions in immune responses. In some embodiments, Th1-type cytokines can be induced, and thus, the immunostimulatory compositions of the present invention can promote a Th1 type antigen-specific immune response including cytotoxic T-cells (e.g., thereby avoiding unwanted Th2 type immune responses (e.g., generation of Th2 type cytokines (e.g., IL-13) involved in enhancing the severity of disease (e.g., IL-13 induction of mucus formation))).

Cytokines play a role in directing the T cell response. Helper (CD4+) T cells orchestrate the immune response of mammals through production of soluble factors that act on other immune system cells, including B and other T cells.

Most mature CD4+T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

Thus, in preferred embodiments, the present invention provides a method of stimulating a Th1-type immune response in a subject comprising administering to a subject a composition comprising an immunogen. However, in other embodiments, the present invention provides a method of stimulating a Th2-type immune response in a subject (e.g., if balancing of a T cell mediated response is desired) comprising administering to a subject a composition comprising an immunogen. In further preferred embodiments, adjuvants can be used (e.g., can be co-administered with a composition of the present invention) to skew an immune response toward either a Th1 or Th2 type immune response. For example, adjuvants that induce Th2 or weak Th1 responses include, but are not limited to, alum, saponins, and SB-As4. Adjuvants that induce Th1 responses include but are not limited to MPL, MDP, ISCOMS, IL-12, IFN-γ, and SB-AS2.

Several other types of Th1-type immunogens can be used (e.g., as an adjuvant) in compositions and methods of the present invention. These include, but are not limited to, the following. In some embodiments, monophosphoryl lipid A (e.g., in particular 3-de-O-acylated monophosphoryl lipid A (3D-MPL)), is used. 3D-MPL is a well known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 µm in diameter, described in EP 0 689 454, hereby incorporated by reference in its entirety).

In some embodiments, saponins are used as an immunogen (e.g.,Th1-type adjuvant) in a composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree Quillaj a Saponaria Molina), and fractions thereof (See, e.g., U.S. Pat. No. 5,057,540; Kensil, Crit Rev Ther Drug Carrier Syst, 1996, 12 (1-2): 1-55; and EP 0 362 279, each of which is hereby incorporated by reference in its entirety). Also contemplated to be useful in the present invention are the haemolytic saponins QS7, QS17, and QS21 (HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also contemplated to be useful are combinations of QS21 and polysorbate or cyclodextrin (See, e.g., WO 99/10008, hereby incorporated by reference in its entirety.

In some embodiments, an immunogenic oligonucleotide containing unmethylated CpG dinucleotides ("CpG") is used as an adjuvant. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into a composition of the present invention for inducing an immune response. In some embodiments, a free solution of CpG is co-administered together with an antigen (e.g., present within a solution (See, e.g., WO 96/02555; hereby incorporated by reference). In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. AcadSci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an E. Coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and other immunogenic substances (e.g., that enhance the effectiveness of a composition of the present invention) are used with a composition comprising an immunogen of the present invention.

Additional examples of adjuvants that find use in the present invention include poly(di(carboxylatophenoxy) phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

Adjuvants may be added to a composition comprising an immunogen, or, the adjuvant may be formulated with carriers, for example liposomes, or metallic salts (e.g., aluminium salts (e.g., aluminium hydroxide)) prior to combining with or co-administration with a composition.

In some embodiments, a composition comprising an immunogen comprises a single adjuvant. In other embodiments, a composition comprises two or more adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, a composition comprising an immunogen comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. Although an understanding of the mechanism is not necessary to practice the present invention and the present invention is not limited to any particular mechanism of action, in some embodiments, use of a mucoadhesive (e.g., in a composition comprising an immunogen) enhances induction of an immune response in a subject (e.g., administered a composition of the present invention) due to an increase in duration and/or amount of exposure to an immunogen that a subject experiences when a mucoadhesive is used compared to the duration and/or amount of exposure to an immunogen in the absence of using the mucoadhesive.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

A composition comprising an immunogen of the present invention can be used therapeutically (e.g., to enhance an immune response) or as a prophylactic (e.g., for immunization (e.g., to prevent signs or symptoms of disease)). A composition comprising an immunogen of the present invention can be administered to a subject via a number of different delivery routes and methods.

For example, the compositions of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Illum et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science and Practice of Pharmacy, Mack Publishing Company, Easton, Pa., 19th edition, 1995). The present invention is not limited by the route of administration.

Although an understanding of the mechanism is not necessary to practice the present invention and the present invention is not limited to any particular mechanism of action, in some embodiments, mucosal vaccination is the preferred route of administration as it has been shown that mucosal administration of antigens has a greater efficacy of inducing protective immune responses at mucosal surfaces (e.g., mucosal immunity), the route of entry of many pathogens. In addition, mucosal vaccination, such as intranasal vaccination, may induce mucosal immunity not only in the nasal mucosa, but also in distant mucosal sites such as the genital mucosa (See, e.g., Mestecky, Journal of Clinical Immunology, 7:265-276, 1987). More advantageously, in further preferred embodiments, in addition to inducing mucosal immune responses, mucosal vaccination also induces systemic immunity. In some embodiments, non-parenteral administration (e.g., muscosal administration of vaccines) provides an efficient and convenient way to boost systemic immunity (e.g., induced by parenteral or mucosal vaccination (e.g., in cases where multiple boosts are used to sustain a vigorous systemic immunity)).

In some embodiments, a composition comprising an immunogen of the present invention may be used to protect or treat a subject susceptible to, or suffering from, disease by means of administering a composition of the present invention via a mucosal route (e.g., an oral/alimentary or nasal route). Alternative mucosal routes include intravaginal and intra-rectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized composition is provided. Enteric formulations such as gastro resistant capsules for oral administration, suppositories for rectal or vaginal administration also form part of this invention. Compositions of the present invention may also be administered via the oral route. Under these circumstances, a composition comprising an immunogen may comprise a pharmaceutically acceptable excipient and/or include alkaline buffers, or enteric capsules. Formulations for nasal delivery may include those with dextran or cyclodextran and saponin as an adjuvant.

Compositions of the present invention may also be administered via a vaginal route. In such cases, a composition comprising an immunogen may comprise pharmaceutically acceptable excipients and/or emulsifiers, polymers (e.g., CARBOPOL), and other known stabilizers of vaginal creams and suppositories. In some embodiments, compositions of the present invention are administered via a rectal route. In such cases, compositions may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response.

For example, in some embodiments, a composition comprising an immunogen is administered to a mucosal surface of a subject in either a priming or boosting vaccination regime. Alternatively, in some embodiments, the composition is administered systemically in either a priming or boosting vaccination regime. In some embodiments, a composition comprising an immunogen is administered to a subject in a priming vaccination regimen via mucosal administration and a boosting regimen via systemic administration. In some embodiments, a composition comprising an immunogen is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. A composition comprising an immunogen may be used for both prophylactic and therapeutic purposes.

In some embodiments, compositions of the present invention are administered by pulmonary delivery. For example, a composition of the present invention can be delivered to the lungs of a subject (e.g., a human) via inhalation (e.g., thereby traversing across the lung epithelial lining to the blood stream (See, e.g., Adjei, et al. Pharmaceutical Research 1990; 7:565-569; Adjei, et al. Int. J. Pharmaceutics 1990; 63:135-144; Braquet, et al. J. Cardiovascular Pharmacology 1989 143-146; Hubbard, et al. (1989) Annals of Internal Medicine, Vol. III, pp. 206-212; Smith, et al. J. Clin. Invest. 1989; 84:1145-1146; Oswein, et al. "Aerosolization of Proteins", 1990; Proceedings of Symposium on Respiratory Drug Delivery II Keystone, Colo.; Debs, et al. J. Immunol. 1988; 140:3482-3488; and U.S. Pat. No. 5,284,656 to Platz, et al, each of which are hereby incorporated by reference in its entirety). A method and composition for pulmonary delivery of drugs for systemic effect is described in U.S. Pat. No. 5,451,569 to Wong, et al., hereby incorporated by reference; See also U.S. Pat. No. 6,651,655 to Licalsi et al., hereby incorporated by reference in its entirety)).

Further contemplated for use in the practice of this invention are a wide range of mechanical devices designed for pulmonary and/or nasal mucosal delivery of pharmaceutical agents including, but not limited to, nebulizers, metered dose inhalers, and powder inhalers, all of which are familiar to those skilled in the art. Some specific examples of commercially available devices suitable for the practice of this invention are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). All such devices require the use of formulations suitable for dispensing of the therapeutic agent. Typically, each formulation is specific to the type of device employed and may involve the use of an appropriate propellant material, in addition to the usual diluents, adjuvants, surfactants, carriers and/or other agents useful in therapy. Also, the use of liposomes, microcapsules or microspheres, inclusion complexes, or other types of carriers is contemplated.

Thus, in some embodiments, a composition comprising an immunogen of the present invention may be used to protect and/or treat a subject susceptible to, or suffering from, a disease by means of administering the composition by mucosal, intramuscular, intraperitoneal, intradermal, transdermal, pulmonary, intravenous, subcutaneous or other route of administration described herein. Methods of systemic administration of the vaccine preparations may include conventional syringes and needles, or devices designed for ballistic delivery of solid vaccines (See, e.g., WO 99/27961, hereby incorporated by reference), or needle-less pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). The present invention may also be used to enhance the immunogenicity of antigens applied to the skin (transdermal or transcutaneous delivery, See, e.g., WO 98/20734; WO 98/28037, each of which are hereby incorporated by reference). Thus, in some embodiments, the present invention provides a delivery device for systemic administration, pre-filled with the vaccine composition of the present invention.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., *E. coli*). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non-human mammals (e.g., pigs, cattle, goats, horses, sheep, or other livestock; or mice, rats, rabbits or other animal). In some embodiments, compositions and methods of the present invention are utilized in research settings (e.g., with research animals).

A composition of the present invention may be formulated for administration by any route, such as mucosal, oral, transdermal, intranasal, parenteral or other route described herein. The compositions may be in any one or more different forms including, but not limited to, tablets, capsules, powders, granules, lozenges, foams, creams or liquid preparations.

Topical formulations of the present invention may be presented as, for instance, ointments, creams or lotions, foams, and aerosols, and may contain appropriate conventional additives such as preservatives, solvents (e.g., to assist penetration), and emollients in ointments and creams.

Topical formulations may also include agents that enhance penetration of the active ingredients through the skin. Exemplary agents include a binary combination of N-(hydroxyethyl) pyrrolidone and a cell-envelope disordering compound, a sugar ester in combination with a sulfoxide or phosphine oxide, and sucrose monooleate, decyl methyl sulfoxide, and alcohol.

Other exemplary materials that increase skin penetration include surfactants or wetting agents including, but not limited to, polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulfosuccinate; and sodium sarcosinate (Sarcosyl NL-97); and other pharmaceutically acceptable surfactants.

In certain embodiments of the invention, compositions may further comprise one or more alcohols, zinc-containing compounds, emollients, humectants, thickening and/or gelling agents, neutralizing agents, and surfactants. Water used in the formulations is preferably deionized water having a neutral pH. Additional additives in the topical formulations include, but are not limited to, silicone fluids, dyes, fragrances, pH adjusters, and vitamins. Topical formulations may also contain compatible conventional carriers, such as cream or ointment bases and ethanol or oleyl alcohol for lotions. Such carriers may be present as from about 1% up to about 98% of the formulation. The ointment base can comprise one or more of petrolatum, mineral oil, ceresin, lanolin alcohol, panthenol, glycerin, bisabolol, cocoa butter and the like.

In some embodiments, pharmaceutical compositions of the present invention may be formulated and used as foams. Pharmaceutical foams include formulations such as, but not limited to, emulsions, microemulsions, creams, jellies and liposomes. While basically similar in nature these formulations vary in the components and the consistency of the final product. The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, preferably do not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) that do not deleteriously interact with the immunogen or other components of the formulation. In some embodiments, immunostimulatory compositions of the present invention are administered in the form of a pharmaceutically acceptable salt. When used the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include, but are not limited to, acetic acid and a salt (1-2% w/v); citric acid and a salt (1-3% w/v); boric acid and a salt (0.5-2.5% w/v); and phosphoric acid and a salt (0.8-2% w/v). Suitable preservatives may include benzalkonium chloride (0.003-0.03% w/v); chlorobutanol (0.3-0.9% w/v); parabens (0.01-0.25% w/v) and thimerosal (0.004-0.02% w/v).

In some embodiments, vaccine compositions are co-administered with one or more antibiotics. For example, one or more antibiotics may be administered with, before and/or after administration of the composition. The present invention is not limited by the type of antibiotic co-administered. Indeed, a variety of antibiotics may be co-administered including, but not limited to, β-lactam antibiotics, penicillins (such as natural penicillins, aminopenicillins, penicillinase-resistant penicillins, carboxy penicillins, ureido penicillins), cephalosporins (first generation, second generation, and third generation cephalosporins), and other β-lactams (such as imipenem, monobactams,), β-lactamase inhibitors, vancomycin, aminoglycosides and spectinomycin, tetracyclines, chloramphenicol, erythromycin, lincomycin, clindamycin, rifampin, metronidazole, polymyxins, doxycycline, quinolones (e.g., ciprofloxacin), sulfonamides, trimethoprim, and quinolines.

There are an enormous amount of antimicrobial agents currently available for use in treating bacterial, fungal and viral infections. For a comprehensive treatise on the general classes of such drugs and their mechanisms of action, the skilled artisan is referred to Goodman & Gilman's "The Pharmacological Basis of Therapeutics" Eds. Hardman et al., 9th Edition, Pub. McGraw Hill, chapters 43 through 50, 1996, (herein incorporated by reference in its entirety). Generally, these agents include agents that inhibit cell wall synthesis (e.g., penicillins, cephalosporins, cycloserine, vancomycin, bacitracin); and the imidazole antifungal agents (e.g., miconazole, ketoconazole and clotrimazole); agents that act directly to disrupt the cell membrane of the microorganism (e.g., detergents such as polmyxin and colistimethate and the antifungals nystatin and amphotericin B); agents that affect the ribosomal subunits to inhibit protein synthesis (e.g., chloramphenicol, the tetracyclines, erthromycin and clindamycin); agents that alter protein synthesis and lead to cell death (e.g., aminoglycosides); agents that affect nucleic acid metabolism (e.g., the rifamycins and the quinolones); the antimetabolites (e.g., trimethoprim and sulfonamides); and the nucleic acid analogues such as zidovudine, gangcyclovir, vidarabine, and acyclovir which act to inhibit viral enzymes essential for DNA synthesis. Various combinations of antimicrobials may be employed.

The present invention also includes methods involving co-administration of a vaccine composition comprising an immunogen with one or more additional active and/or immunostimulatory agents (e.g., a composition comprising a different immunogen, an antibiotic, anti-oxidant, etc.). Indeed, it is a further aspect of this invention to provide methods for enhancing prior art immunostimulatory methods (e.g., immunization methods) and/or pharmaceutical compositions by co-administering a composition of the present invention. In co-administration procedures, the agents may be administered concurrently or sequentially. In one embodiment, the compositions described herein are administered prior to the other active agent(s). The pharmaceutical formulations and modes of administration may be any of those described herein. In addition, the two or more co-administered agents may each be administered using different modes (e.g., routes) or different formulations. The additional agents to be co-administered (e.g., antibiotics, adjuvants, etc.) can be any of the well-known agents in the art, including, but not limited to, those that are currently in clinical use.

In some embodiments, a composition comprising an immunogen is administered to a subject via more than one route. For example, a subject that would benefit from having a protective immune response (e.g., immunity) towards a pathogenic microorganism may benefit from receiving mucosal administration (e.g., nasal administration or other mucosal routes described herein) and, additionally, receiving one or more other routes of administration (e.g., parenteral or pulmonary administration (e.g., via a nebulizer, inhaler, or other methods described herein). In some preferred embodiments, administration via mucosal route is sufficient to induce both mucosal as well as systemic immunity towards an immunogen or organism from which the immunogen is derived. In other embodiments, administration via multiple routes serves to provide both mucosal and systemic immunity. Thus, although an understanding of the mechanism is not necessary to practice the present invention and the present invention is not limited to any particular mechanism of action, in some embodiments, it is contemplated that a subject administered a composition of the present invention via multiple routes of administration (e.g., immunization (e.g., mucosal as well as airway or parenteral administration of the composition) may have a stronger immune response to an immunogen than a subject administered a composition via just one route.

Other delivery systems can include time-release, delayed release or sustained release delivery systems. Such systems can avoid repeated administrations of the compositions, increasing convenience to the subject and a physician. Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109, hereby incorporated by reference. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, each of which is hereby incorporated by reference and (b) diffusional systems in which an active component permeates at a controlled rate from a polymer such as described in U.S. Pat. Nos. 3,854,480, 5,133,974 and 5,407,686, each of which is hereby incorporated by reference. In addition, pump-based hardware delivery systems can be used, some of which are adapted for implantation.

In some embodiments, a vaccine composition of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising 0.5-50% of a nanemulsion and immunogen present in the concentrated composition. Concentrated compositions are contemplated to be useful in a setting in which large numbers of subjects may be administered a composition of the present invention (e.g., an immunization clinic, hospital, school, etc.). In some embodiments, a composition comprising an immunogen of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eights, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing albumin variant, immunogens, and other components and for screening for new components. Thus, it is not intended that the present invention be limited to any particular subject and/or application setting.

The present invention further provides kits comprising the vaccine compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

EXAMPLE 1

Engineering of Albumin Variants

Material and Method
Construction of Expression Vectors Encoding Albumin Variants The pcDNA3 vector (Invitrogen) was used for cloning of cDNAs encoding mouse and human albumin variants fused to a cDNA segment encoding GST. All vectors also encode Epstein-Barr virus origin of replication (OriP), as previously described (Andersen et al., Clinical biochemistry 43, 367-372 (2010); Berntzen, et al. Journal of immunological methods 298, 93-104 (2005)). cDNA fragments encoding the MSA and HSA genes (Table 1) were all ordered and obtained in pUC57 vectors from GenScript Inc (N.J., USA). The pUC57 vectors were flanked by the restriction sites HindIII and XhoI. A DNA sequence encoding a glycine-serine (GS) stretch of amino acids ((GGS)4GG) was N-terminally fused The GST sequence. The vectors pcDNA3-HSAwt-GST-OriP and pcDNA3-HSAbartin-GST-OriP have previously been described (Andersen et al., 2010, supra).
Production of Albumin Variants Transient transfection of adherent HEK293E cells was done using polyethyleneimine (PEIMax; MW 4000; Polysciences, Inc, Warrington). Prior to transfection, cells were grown to 95% confluence in T175 bottles (50 ml). 62.5 µg of plasmid DNA was mixed with 3.75 ml of OptiMEM medium (Invitrogen) (solution 1) and 25 µl of PEI-MAX (6.45 mg/ml) and 3.75 ml of dH2O. Solution 1 and 2 were then mixed, followed by incubation for 30 minutes at RT before the mixture was added to the seeded cells. The supernatants were harvested every second day for up to 12 days post transfection.

A GSTrap FF column (GE Healthcare, UK) was used to purify the GST-tagged MSA and HSA variants. The column was coupled to a BioLogic workstation and recorder (BIO-RAD), and purification was done in accordance with the manufacturer's protocol. Briefly, 100 ml of 1×PBS/0.05% sodium azide (pH 7.2) was used to pre-equilibrate the column before supernatant was sterile filtrated with a 0.22 µm vacuum filter (Corning) with 0.05% sodium azide was applied with a flow-rate of 1-2 ml/min. Then, 200 ml of 1×PBS/0.05% azide was applied to wash out unspecific binding. Bound GST-fusions were eluted with 50 ml of 10 mM reduced glutathione (Sigma-Aldrich) diluted in 50 mM of Tris-HCl (pH 8.0). Eluted fractions were collected, upconcentrated and buffer-changed to 1×PBS/0.05% azide using Amicon Ultra-10 columns (Millipore). All fractions were stored in −20° C. with a concentration of 0.5-1 mg/ml. The column was washed and stored in 20% ethanol at 4° C.
Production of Mouse and Human FcRn Truncated monomeric His-tagged mouse and human FcRn (mFcRn and hFcRn) were produced using a Baculovirus expression vector system, essentially as previously described (Kim et al., European journal of immunology 29, 2819-2825 (1999); Popov, S. et al. Molecular immunology 33, 521-530 (1996)). The receptors were purified using a HisTrap HP column supplied with $Ni^{2+}$ ions (GE Healthcare, UK). Prior to use, the column was pre-equilibrated with 1×PBS containing 0.05% sodium azide. The pH of the supernatant was adjusted with 1×PBS/0.05% sodium azide (pH 10.9) to pH 7.2, before applied to the HisTrap HP column with a flow rate of 5 ml $min^{-1}$. After washing with 200 ml of 1×PBS followed by 50 ml of 25 mM imidazole/1×PBS, bound receptor was eluted with 50 ml of 250 mM imidazole/1×PBS (pH 7.2-7.4). The protein was up-concentrated and buffer-changed to 1×PBS using Amicron Ultra-10 columns (Millipore) before applied on a HiLoad 26/600 Superdex 200 prep grade column (GE Healthcare) following the manufactures protocol. Eluted fractions were pooled and up-concentrated using Amicon Ultra columns (Millipore) and stored at 4° C.
Enzyme-Linked Immunosorbent Assay (ELISA)

Rabbit IgG (10 µg/ml) (Southern Biotech) was coated in microtiter wells (Nunc), and incubated over night at 4° C. Then wells were blocked with PBS/4% skim milk for 1 hour at room temperature, and washed 4 times in PBS/0.005% Tween20 (PBS/T) pH 6.0. Soluble mFcRn or hFcRn (20 µg/ml) was diluted in PBS/T/4% skimmed milk pH 6.0, added to the wells, and incubated for 1.5 hours at room temperature, prior to washing as described above. Subsequently, the GST-tagged albumin variants (5 µg/ml) were diluted in PBS/T/4% skimmed milk pH 6.0 and added to the wells for 2 hours at room temperature. After washing as above, a horseradish peroxidase-conjugated anti-GST antibody (GE Healthcare), diluted (1:4000) in PBS/T/4% skimmed milk pH 6.0, was added and incubated for 1 hour. Subsequently, the wells were washed as above and bound albumin variants were detected using tetramethylbenzidine substrate (Calbiochem). The absorbance was measured at 450 nm after adding of 100 µl of 1 M HCl using the Sunrise spectophotometer (TECAN).
Surface Plasmon Resonance (SPR)

SPR experiments were performed on a BIAcore 3000 instrument (GE Healthcare) and amine coupling (GE Healthcare) was used for immobilization of GST-fused albumin variants on CMS chips. 2 µg/ml of each was injected in 10 mM sodium acetate at pH 5.0 (GE Healthcare), essentially as described by the manufacturer. Unreacted moieties on the chip surfaces were blocked with 1 M ethanolamine. Experiments were done with phosphate buffers (67 mm phosphate buffer, 0.15 M NaCl, 0.005% Tween 20) at pH 6.0 or 7.4) for both running or dilution of samples. Kinetic measurements were performed by injecting serial dilutions of monomeric His-tagged hFcRn (1.0-0.015 µM) over immobilized albumin variants at pH 6.0 or 7.4, with a flow rate of 50 µL/min at 25° C. Kinetic rate values were calculated using the simple Langmuir 1:1 ligand binding model provided by the BIAevaluation 4.1 software. The closeness of the fit, described by the statistical value $\chi^2$, which represents the mean square, was lower than 2.0 in all affinity estimations. To correct for nonspecific binding and bulk buffer effects, binding responses obtained from the control CMS surfaces and blank injections were subtracted from each interaction curve.
T84 Transcytosis Assay The human epithelial cell line T84 (ATCC) was maintained in Dulbecco's modified Eagles Medium DMEM (Invitrogen) and HAM's F-12 medium (1:1) (Invitrogen), supplied with 10% heat inactivated FBS, 2 mM Lg and 50 U/ml PS (all from Bio-Wittaker). The cells were incubated at 37° C. in a humidified 5% $CO_2$, 95% air incubator. Transwell filters (1.12 $cm^2$) with PTFE membrane and 0.4 µm pore size (Corning Costar, Mass., USA) were incubated ON in growth medium before $1.0 \times 10^6$ cells/well were seeded. Transepithelial resistance (TER) where measured daily using a MILLICELL-ERS volt-ohm meter (MILLIPORE). The cells were cultured for 4-6 days before reaching a TER value of 1000-1500Ω×$cm^2$. Growth medium were exchanged daily.

Prior to experiments, the T84 monolayers were washed and incubated for 1 hour in Hank's HBSS buffer (Invitrogen). For measurement of apical to basolateral transport, 200 µl of normalized HSA variants (20-30 µg/ml) was added to the apical side followed by sampling of 400 µl of medium at 0 and 4 hours from the basolateral reservoirs with 500 µl HBSS buffer.

TABLE 1

Constructed vectors encoding albumin variants

| Albumin | DIII mutation | Abbreviation |
|---|---|---|
| HSA | WT | WT |
|  | K573Y | KY |
|  | I523G | IG |
|  | I253A | IA |
|  | T527M | TM |
|  | E505Q | EQ |
|  | K573P | KP |
|  | K573Y/I523G | KY/IG |
|  | K573Y/I523G/T527M | KY/IG/TM |
|  | K573Y/E505Q/T527M | KY/EQ/TM |
|  | K573Y/T527M | KY/TM |
|  | K573P/I523G | KP/IG |
|  | K573P/I523G/T527M | KP/IG/TM |
|  | K573P/E505Q/T527M | KP/EQ/TM |
|  | K573P/T527M | KP/TM |
|  | K500A/H510Q | KA/HQ |
|  | No DIII | Bartin |
| MSA | WT | WT |
|  | K500A/H510Q | KA/HQ |

Results

A range of engineered HSA variants with single point mutations within the C-terminal DIII, with either increased or decreased binding to hFcRn were made. Such HSA variants were constructed based on inspection of a docking model of the hFcRn-HSA complex (Andersen et al., Nature communications 3, 610 2012). Here, a selection of mutations was introduced into DIII of HSA to investigate how either single point mutations or a combination of mutations affected binding to hFcRn. In addition, some of the mutant variants were combined with I523G (WO201211218A1; herein incorporated by reference in their entirety).

Five single mutants; E505Q (EQ), T527M (TM), I523G (IG), K573Y (KY), and K573P (KP), and 10 of these mutations (as listed in Table 1) were introduced into DIII of HSA. In addition to WT HSA were made, a double mutant K500A/H510Q (KA/HQ), were made based on a combination of two point mutations previously shown to greatly reduce binding to hFcRn (Andersen et al., 2012, supra). The mutated amino acids are highlighted in the crystal structure illustrations of HSA in FIG. 2.

Figure 2B:
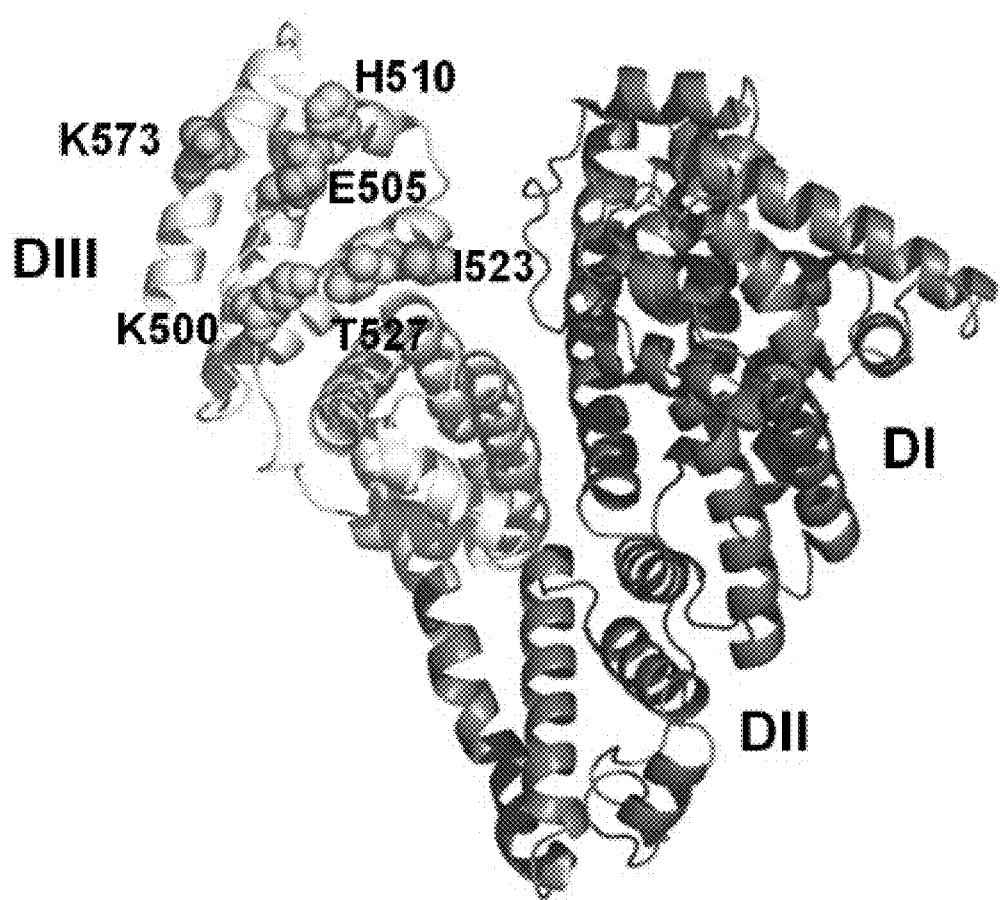

FIG. 2 shows the crystal structure of HSA. The structural location of the amino acid positions mutated within DIII of HSA. The picture shows the overall structural architecture of HSA. The DI-DII and DIII are shown in gray and light gray, respectively, while the positions mutated are highlighted in colored spheres, K500A (KA), H510Q (HQ) (KA/HQ), E505Q (EQ), T527M (TM) I523G (IG), K573Y (KY) and K573P (KP). The illustration was made using the crystallographic data on HSA5, and the program PyMOL.

Figure 3:
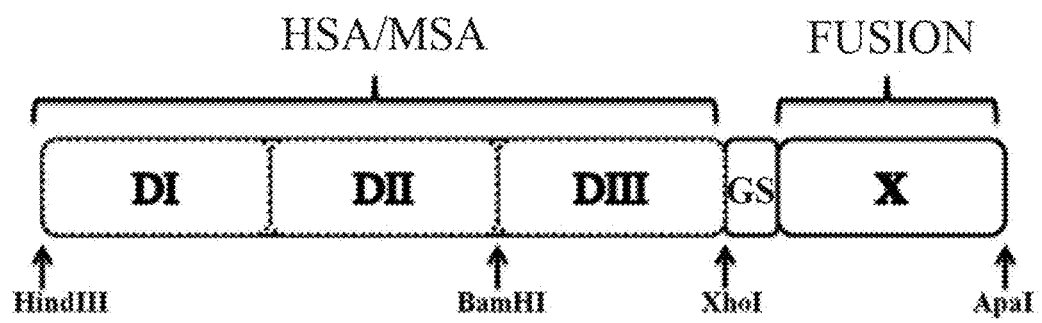

FIG. 3 shows a schematic overview of the cloning cassette for construction of albumin with C-terminal fused antigen. The cDNA encoding full-length albumin was sub-cloned into the restriction sites HindIII and XhoI, while cDNA fragments encoding only the DIII segment were sub-cloned onto the restriction sites BamHI and XhoI. A BamHI restriction site was introduction into the albumin cDNA sequences by silence mutation to allow for DIII sub-cloning. A GS-linker sequence was introduced between the cDNA encoding albumin and the fused GST protein. The cDNA encoding the antigen was sub-cloned onto the restriction sites XhoI and ApaI.

Figure 4A:
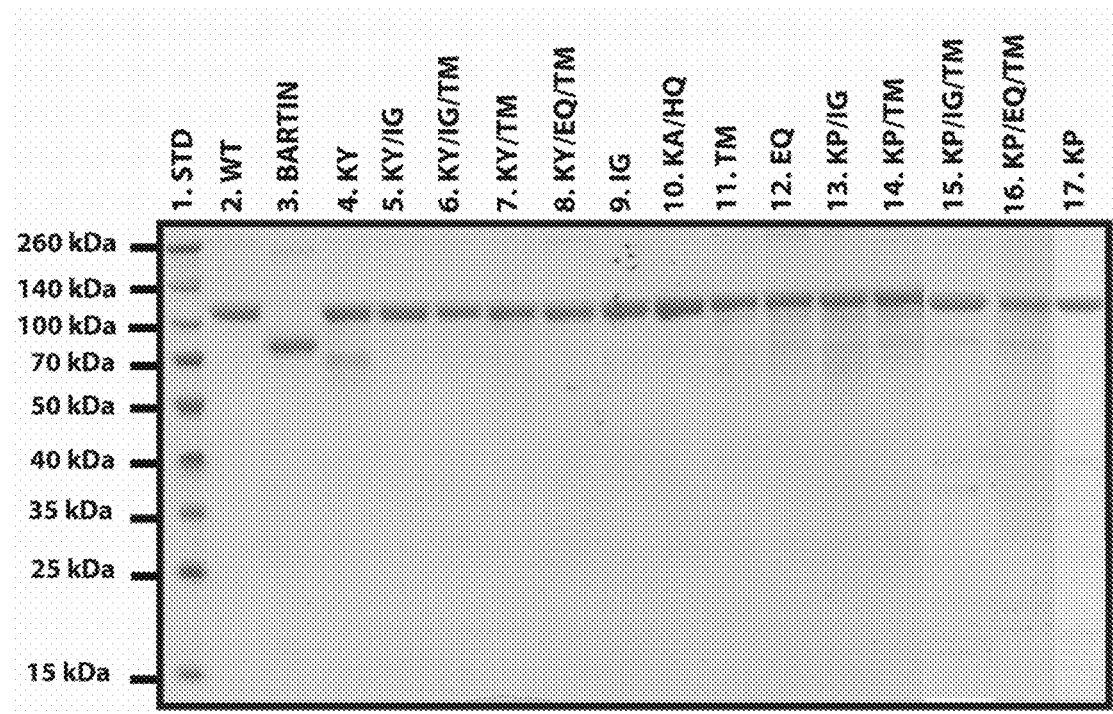
Figure 4B:
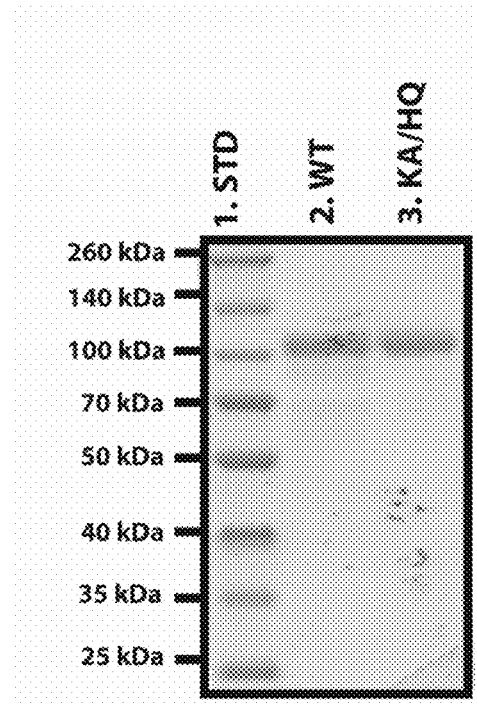

FIG. 4 shows SDS-PAGE analysis of purified albumin-GST variants. Representative non-reducing SDS-PAGE gel analyses of (A) HSA-GST variants and (MSA-GST variants). 3 µg of each variant was applied on the gel. HSA and MSA variants were produced by transient transfection of HEK293E cells. In addition to the full-length variants, a truncated HSA variant lacking almost the whole DIII (Bartin), previously shown not to bind hFcRn1, was included. Harvested supernatants were pooled and filtrated before application to a GSTrap FF column. The integrity of the purified variants was analyzed using non-reducing SDS-PAGE followed by Coomassie staining. All variants migrated as major bands corresponding to 100-110 kDa, except for HSA Bartin, that migrated with a molecular weight of roughly 70 kDa, all in accordance with expected molecular weights.

Figure 5A:
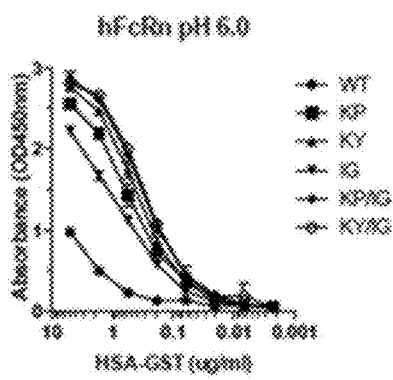
Figure 5B:
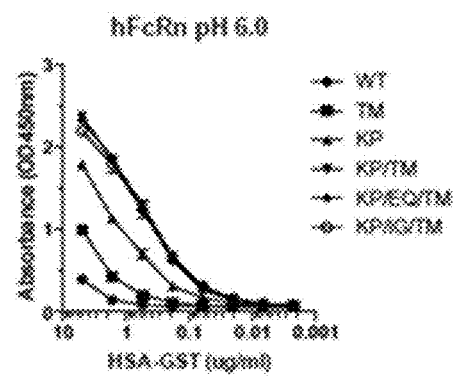
Figure 5C:
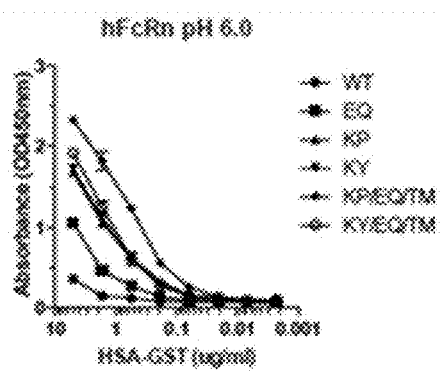
Figure 5D:
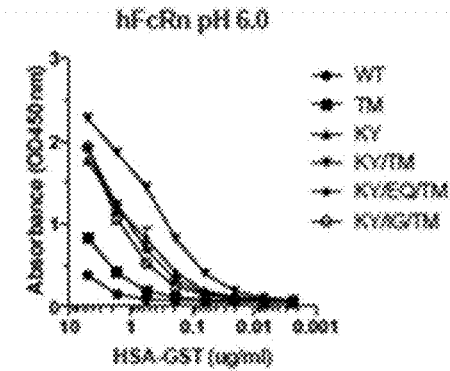
Figure 5E:
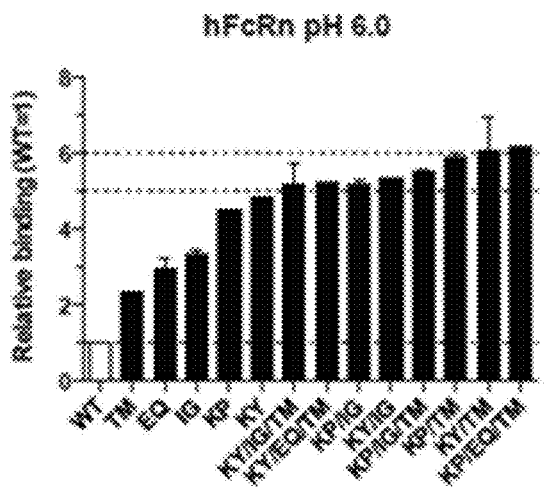

To compare the binding capacities of the albumin fusions at acidic pH, titrated amounts of normalized HSA-GST variants were added to hFcRn captured on rabbit IgG, and bound albumin variants were detected suing an HRP-conjugated anti-GST antibody from goat (FIG. 5A-D). Binding to hFcRn was calculated where binding of WT HSA was set to 1.0 (FIG. 5C). Of the single point mutants, EQ, IG and TM showed moderate improvement in binding, 2-3 folds better than the WT, followed by KP and KY that bound 5 times more strongly than the WT. Combining two or three mutations resulted in further gain of binding, where the mutants KP/IG, KY/EQ/TM and KY/IG/TM showed slightly improved binding compared with KY followed by KY/IG and KP/IG/TM, while the strongest binding were detected for KY/TM, KP/TM and KP/EQ/TM, which showed a 6-fold improvement in binding strength. Thus, among the single mutants, KY and KP bound the strongest, while the combination of these with TM and EQ gave the best binders.

Figure 6A:
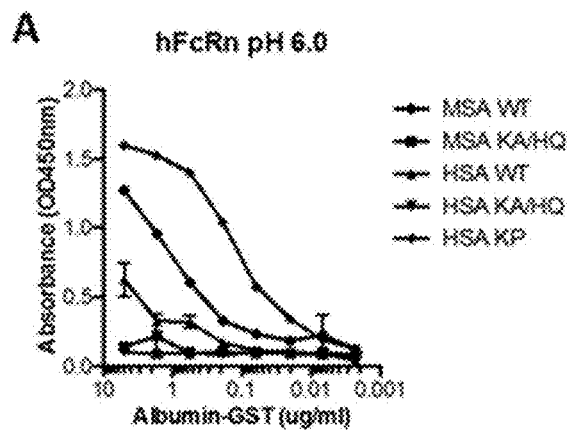
Figure 6B:
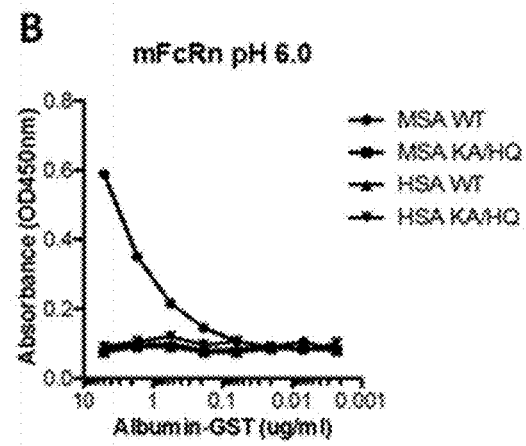
Figure 6C:
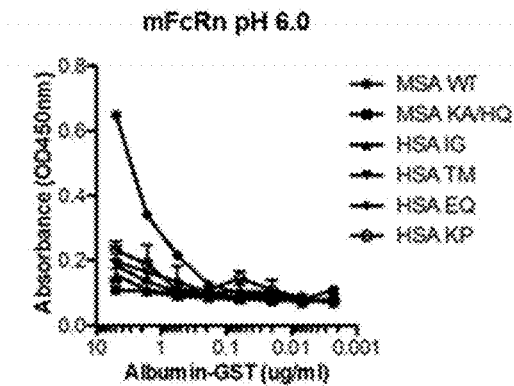
Figure 6D:
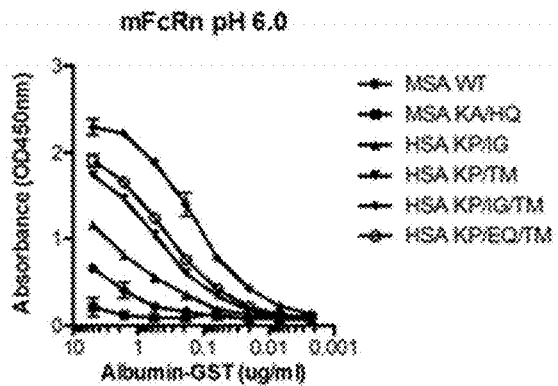

To compare the binding capacities of the albumin fusions at acidic pH, titrated amounts of normalized MSA and HSA-GST variants were added to (FIG. 6A) hFcRn and (FIG. 6B-D) mFcRn captured on rabbit IgG, and bound albumin variants were detected suing an HRP-conjugated anti-GST antibody from goat.

Binding to hFcRn (FIG. 6A) and mFcRn (FIGS. 6B-D) was calculated where binding of WT MSA was set to 1.0 (FIG. 7). KP was shown to bind 3-fold stronger than MSA to hFcRn, and the receptor bound stronger to MSA than to HSA. HSA and MSA KA/HQ mutants did not bind to hFcRn or mFcRn. In addition, no detectable binding was seen for mFcRn towards HSA. Of the single point mutants, none of them bound stronger than MSA to mFcRn, while the combination of KP with IG resulted in a moderate improvement in binding, 2 fold better than WT MSA. Furthermore, the following combinations KP/TM, KP/IG/TM and KP/EQ/TM gained 4-6 times improvement in relative binding compared with WT MSA.

The sensorgrams (FIG. 8) show large differences in binding to hFcRn at acidic pH. The binding curves were fitted to a 1:1 binding model and the derived binding kinetics are listed in Table 2. Here, fusion to GST was shown to only have a very minor negative impact on binding to hFcRn, as in agreement with previous results (Andersen et al., J Biol Chem. 2013 Aug. 16; 288(33):24277-85). The EQ and IG mutants were shown to bind more than 6-fold better to hFcRn than the WT counterpart, while IA bound nearly as good as these mutants. Furthermore, the KP mutant bound with a 14-fold improvement while the triple mutant EQ/TM/KP showed the largest improvement, corresponding to more than 180-fold.

Figure 9:
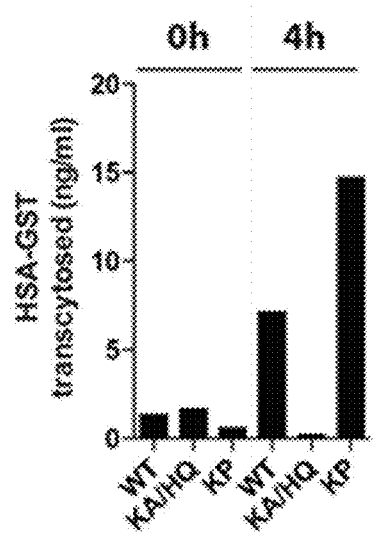

The ability of FcRn to transport IgG across epithelial barriers is well established (Dickinson et al., 1999; McCarthy et al., 2000). However, whether or not FcRn expressed in epithelial cells can transport HSA has not been demonstrated. Thus, to investigate whether HSA could be transported in an FcRn-dependent fashion across an epithelial layer that express endogenous hFcRn, a Tanswell system was used to measure FcRn-mediated IgG transport. First, WT HSA was compared with KA/HQ, and equal amounts of these were added to the apical reservoirs of a Transwell system, where the human epithelia cell line T84 was grown as polarized monolayers. Samples were collected from the basolateral reservoir at time points 0 and 4 hours post addition to the apical side. Transported HSA fusions were quantified using the ELISA where the fusions are captured on an anti-GST antibody and bound fusions are detected using an HRP-conjugated anti-HSA antibody. A striking difference in transport efficacy was detected, as 5-fold more of the WT fusion was transported than the double mutant lacking binding to hFcRn (FIG. 9). Thus, these data strongly support that FcRn expressed in human epithelium is capable of transcytose HSA across the cellular layer.

Next, it was assessed whether or not a HSA variant with improved binding to hFcRn was transcytosed more efficiently than its WT counterpart. It was found that introduction of the single KP mutation increased the transport efficacy by almost 3-fold compared with the WT (FIG. 9).

TABLE 2

SPR derived kinetics for binding of HSA fusion variants to hFcRn

| HSA variants | Ka ($10^4$/Ms) | Kd ($10^{-3}$/s) | KD (nM) |
| --- | --- | --- | --- |
| WT | 4.3 ± 0.1 | 5.4 ± 0.1 | 125.6 |
| WT-GST | 3.2 ± 0.1 | 4.7 ± 0.2 | 146.8 |
| EQ-GST | 3.9 ± 0.1 | 0.9 ± 0.0 | 23.1 |
| IG-GST | 3.8 ± 0.2 | 0.9 ± 0.0 | 23.6 |
| IA-GST | 4.2 ± 0.1 | 1.2 ± 0.2 | 29.0 |
| KP-GST | 2.9 ± 0.0 | 0.3 ± 0.1 | 10.3 |
| EQ/TM/KP-GST | 12.9 ± 0.1 | 0.1 ± 0.1 | 0.8 |

The kinetic rate constants were obtained using a simple first-order (1:1) Langmuir bimolecular interaction model. The kinetic values represent the average of triplicates.

Example 2

Engineered HSA variants with point mutations within the C-terminal DIII, with either increased binding to hFcRn were. The HSA variants were constructed based on inspection of a docking model of the hFcRn-HSA complex1, and V547 (as described by Eleven Biopharmaceuticals (WO 2013075066 A2). Here, a combination of mutations was introduced into DIII of HSA to investigate how they affected binding to hFcRn.

Materials and Methods

Construction of Expression Vectors Encoding Albumin Variants

The pcDNA3 vector (Invitrogen) was used for cloning of cDNAs encoding human serum albumin variants fused to a cDNA segment encoding GST. All vectors also encode Epstein-Barr virus origin of replication (OriP), as previously described (Andersen et al., 2010, supra; Berntzen et al., supra). cDNA fragments encoding the HSA genes were all ordered and obtained in pUC57 vectors from GenScript Inc (N.J., USA). The pUC57 vectors were flanked by the restriction sites HindIII and XhoI. A DNA sequence encoding a glycine-serine (GS) stretch of amino acids ((GGS)4GG) was N-terminally fused The GST sequence. The vector pcDNA3-HSAwt-GST-OriP has previously been described (Andersen et al., 2010, supra).

Production of Albumin Variants

Transient transfection of adherent HEK293E cells was done using polyethyleneimine (PEIMax; MW 4000; Polysciences, Inc, Warrington). Prior to transfection, cells were grown to 95% confluence in T175 bottles (50 ml). 62.5 µg of plasmid DNA was mixed with 3.75 ml of OptiMEM medium (Invitrogen) (solution 1) and 25 µl of PEI-MAX (6.45 mg/ml) and 3.75 ml of dH2O. Solution 1 and 2 were then mixed, followed by incubation for 30 minutes at RT before the mixture was added to the seeded cells. The supernatants were harvested every second day for up to 12 days post transfection.

A GSTrap FF column (GE Healthcare, UK) was used to purify the GST-tagged HSA variants. The column was coupled to a BioLogic workstation and recorder (BIO-RAD), and purification was done in accordance with the manufacturer's protocol. Briefly, 100 ml of 1×PBS/0.05% sodium azide (pH 7.2) was used to pre-equilibrate the column before supernatant was sterile filtrated with a 0.22 µm vacuum filter (Corning) with 0.05% sodium azide was applied with a flow-rate of 1-2 ml/min. Then, 200 ml of 1×PBS/0.05% azide was applied to wash out unspecific binding. Bound HSA GST-fusions were eluted with 50 ml of 10 mM reduced glutathione (Sigma-Aldrich) diluted in 50 mM of Tris-HCl (pH 8.0). Eluted fractions were collected, upconcentrated and buffer-changed to 1×PBS/0.05% azide using Amicon Ultra-10 columns (Millipore). All fractions were stored in −20° C. with a concentration of 0.5-1 mg/ml. The column was washed and stored in 20% ethanol at 4° C.

Production of Human FcRn

Truncated monomeric His-tagged human FcRn (hFcRn) was produced using a Baculovirus expression vector system, essentially as previously described (Kim et al., supra; Popov et al., supra). The receptors were purified using a HisTrap HP column supplied with $Ni^{2+}$ ions (GE Healthcare, UK). Prior to use, the column was pre-equilibrated with 1×PBS containing 0.05% sodium azide. The pH of the supernatant was adjusted with 1×PBS/0.05% sodium azide (pH 10.9) to pH 7.2, before applied to the HisTrap HP column with a flow rate of 5 ml $min^{-1}$. After washing with 200 ml of 1×PBS followed by 50 ml of 25 mM imidazole/1×PBS, bound receptor was eluted with 50 ml of 250 mM imidazole/1×PBS (pH 7.2-7.4). The protein was up-concentrated and buffer-changed to 1×PBS using Amicron Ultra-10 columns (Millipore) before applied on a HiLoad 26/600 Superdex 200 prep grade column (GE Healthcare) following the manufactures protocol. Eluted fractions were pooled and up-concentrated using Amicon Ultra columns (Millipore) and stored at 4° C.

Surface Plasmon Resonance (SPR)

SPR experiments were performed on a BIAcore 3000 instrument (GE Healthcare) and amine coupling (GE Healthcare) was used for immobilization of GST-fused HSA on CM5 chips. 2 µg/ml of each was injected in 10 mM sodium acetate at pH 5.0 (GE Healthcare), essentially as described by the manufacturer. Unreacted moieties on the chip surfaces were blocked with 1 M ethanolamine. Experiments were done with phosphate buffers (67 mm phosphate buffer, 0.15 M NaCl, 0.005% Tween 20) at pH 6.0 or 7.4) for both running or dilution of samples. Kinetic measurements were performed by injecting serial dilutions of monomeric His-tagged hFcRn (1.0-0.015 µM) over immobilized HSA variants at pH 6.0, with a flow rate of 50 µl/min at 25° C. Kinetic rate values were calculated using the simple Langmuir 1:1 ligand binding model provided by the BIAevaluation 4.1 software. The closeness of the fit, described by the statistical value $\chi^2$, which represents the mean square, was lower than 2.0 in all affinity estimations. To correct for nonspecific binding and bulk buffer effects, binding responses obtained from the control CM5 surfaces and blank injections were subtracted from each interaction curve.
Results

TABLE 3

Binding kinetics of HSA DII mutants toward hFcRn.

| HSA variants[a] | ka ($10^4$/Ms) | kd ($10^{-3}$/s) | KD[b] (nM) |
|---|---|---|---|
| WT | 4.6 ± 0.1 | 6.6 ± 0.1 | 143.4 |
| V547A | 7.4 ± 0.1 | 0.7 ± 0.0 | 9.5 |
| K573P | 2.9 ± 0.0 | 0.3 ± 0.1 | 10.3 |
| V547A/K573P | 12.5 ± 0.5 | 0.09 ± 0.0 | 0.7 |
| E505Q/T527M/ V547A/K573P | 25.0 ± 0.3 | 0.04 ± 0.0 | 0.1 |

Figure 10A:
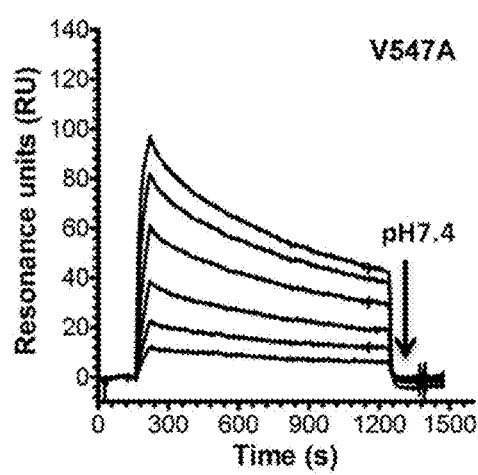
Figure 10B:
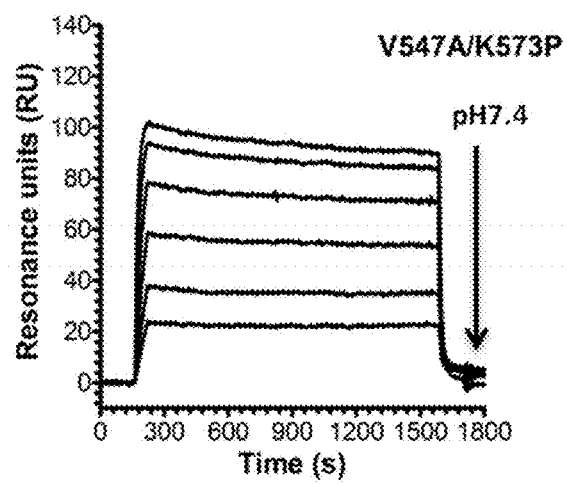
Figure 10C:
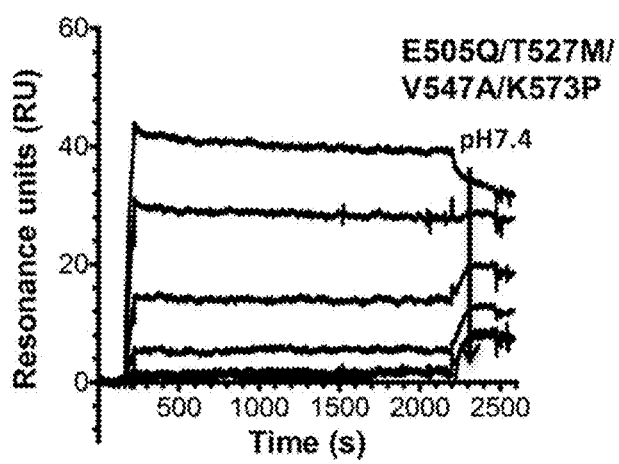
Figure 11A:
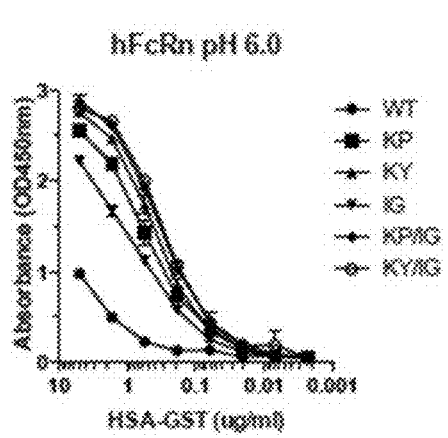
Figure 11B:
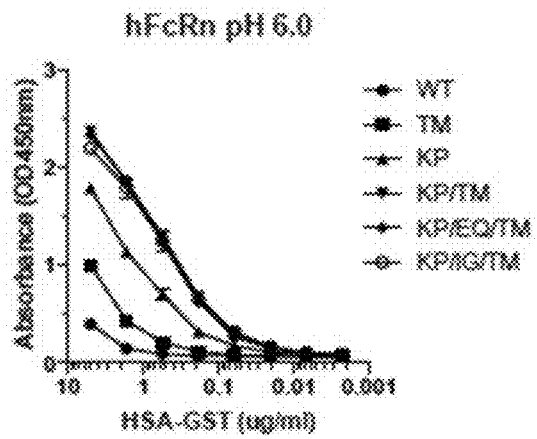
Figure 11C:
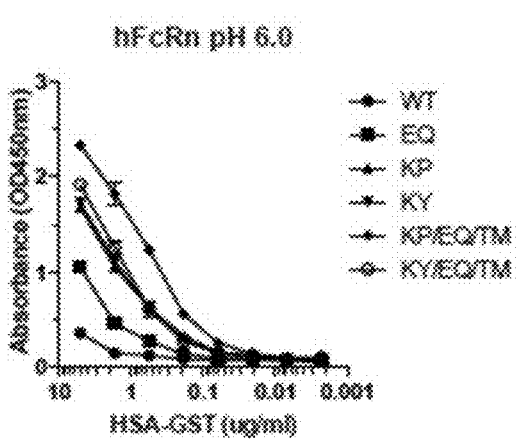
Figure 11D:
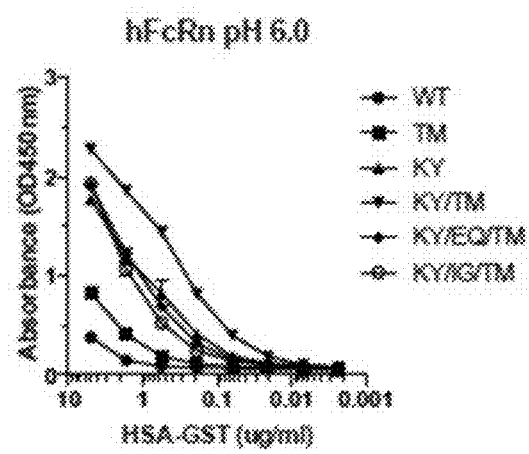
Figure 11E:
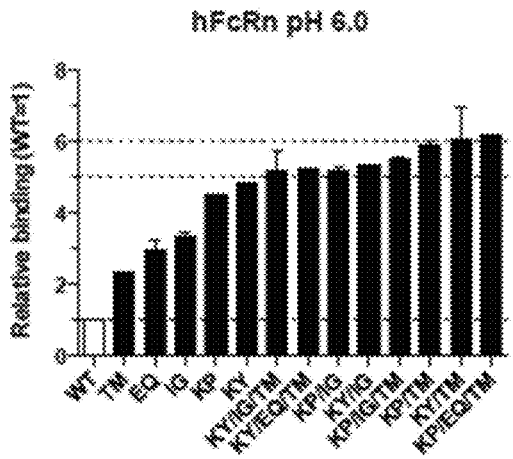
Figure 11F:
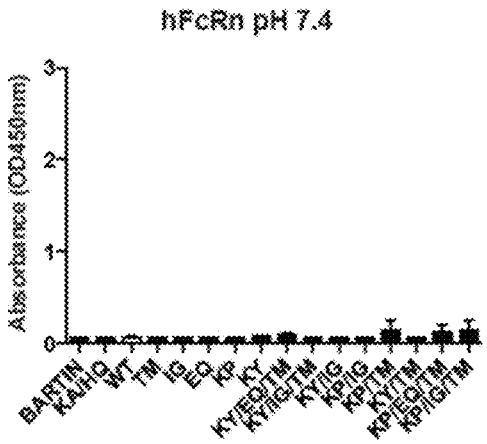
Figure 12A:
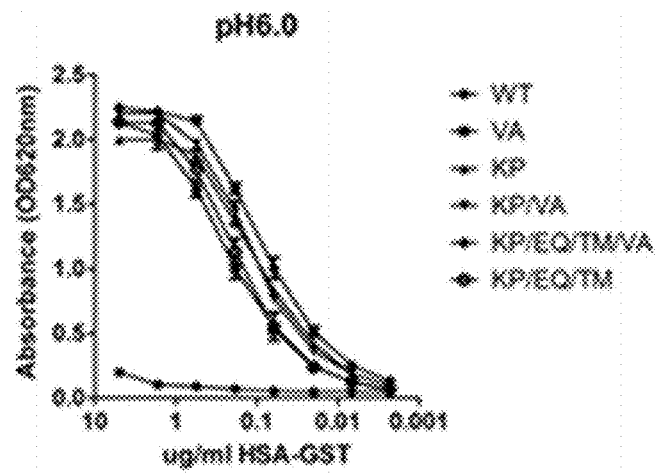
Figure 12B:
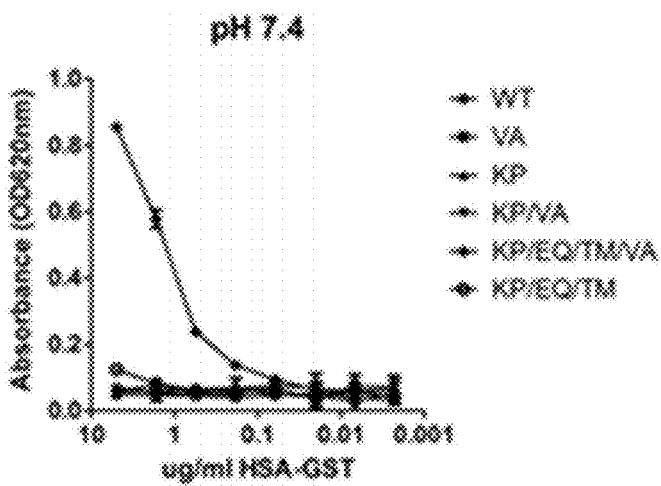

The HSA variants were immobilized (~500 RU) on chips and serial dilutions of hFcRn were injected. The kinetic rate constants were obtained using a simple first-order (1:1) bimolecular interaction model. The kinetic values represent the average of triplicates. Results are shown in Table 3 and FIG. 10.

V547A combined with K573P gave rise to more than 200-fold improved KD compared with WT HSA at pH 6.0, and it binds strictly pH dependent.

V547A combined with E505Q, T527M and K573P gave rise to more than 1400-fold improved KD compared with WT HSA, but it binds less pH dependently.

The Targeted amino acid residues are highlighted in the crystal structure illustration of HSA in FIG. 2.

Example 3

Design of HSA Variants with Altered Binding to hFcRn

A range of engineered HSA variants with single point mutations within the C-terminal DIII, with either increased or decreased binding to hFcRn have been made. Such HSA variants were constructed based on inspection of a docking model of the hFcRn-HSA complex (Andersen et al., Nature communications 3, 610 2012). Here, a selection of mutations was introduced into DIII of HSA to investigate how either single point mutations or a combination of mutations affected binding to hFcRn. In addition, some of the mutant variants were combined with I523G or V547A (WO201211218A1 and WO 2013075066A2; herein incorporated by reference in their entirety).

Six single mutants; E505Q (EQ), T527M (TM), I523G (IG), V547A (VA) K573Y (KY), and K573P (KP), and 10 combinations of these mutations (as listed in Table 4) were introduced into DIII of HSA. In addition to WT HSA were made, a double mutant K500A/H510Q (KA/HQ), were made based on a combination of two point mutations previously shown to greatly reduce binding to hFcRn (Andersen et al., 2012, supra). The mutated amino acids are highlighted in the crystal structure illustrations of HSA in FIG. 2.

TABLE 4

Constructed vectors encoding albumin GST variants

| | DIII mutations | Abbreviations |
|---|---|---|
| HSA mutant variants | K573Y | KY |
| | I523G | IG |
| | I523A | IA |
| | T527M | TM |
| | E505Q | EQ |
| | K573P | KP |
| | K573Y/I523G | KY/IG |
| | K573Y/I523G/T527M | KY/IG/TM |
| | K573Y/E505Q/T527M | KY/EQ/TM |
| | K573Y/T527M | KY/TM |
| | K573P/I523G | KP/IG |
| | K573P/I523G/T527M | KP/IG/TM |
| | K573P/E505Q/T527M | KP/EQ/TM |
| | K573P/T527M | KP/TM |
| | K500A/H510Q | KA/HQ |
| | V547A | VA |
| | K573P/V547A | KP/VA |
| | K573P/E505Q/T527M/V547A | KP/EQ/TM/VA |
| | No DIII | Bartin |

Construction of Expression Vectors Encoding HSA Variants

The pcDNA3 vector (Invitrogen) was used for cloning of cDNAs encoding HSA variants fused to a cDNA segment encoding a GST tag. All vectors also encode Epstein-Barr virus origin of replication (OriP), as previously described (Andersen et al., Clinical biochemistry 43, 367-372; Berntzen et al., (2005) Journal of immunological methods 298, 93-104). cDNA fragments encoding the HSA genes were all ordered and obtained in pUC57 vectors from GenScript Inc (N.J., USA). The pUC57 vectors were flanked by the restriction sites HindIII and XhoI. A DNA sequence encoding a glycine-serine (GS) stretch of amino acids ((GGS)4GG) was N-terminally fused The GST sequence. The vectors pcDNA3-HSAwt-GST-OriP and pcDNA3-HSAbartin-GST-OriP have previously been described (Anderson et al., 2010, supra).

Production of HSA Fusion Variants

Transient transfection of adherent HEK293E cells was done using polyethyleneimine (PEIMax; MW 4000; Polysciences, Inc, Warrington). Prior to transfection, cells were grown to 95% confluence in T175 bottles (50 ml). 62.5 µg of plasmid DNA was mixed with 3.75 ml of OptiMEM medium (Invitrogen) (solution 1) and 25 µl of PEI-MAX (6.45 mg/ml) and 3.75 ml of dH2O. Solution 1 and 2 were then mixed, followed by incubation for 30 minutes at RT before the mixture was added to the seeded cells. The supernatants were harvested every second day for up to 12 days post transfection.

A GSTrap FF column (GE Healthcare, UK) was used to purify the GST-tagged HSA variants. The column was coupled to a BioLogic workstation and recorder (BIO-RAD), and purification was done in accordance with the manufacturer's protocol. Briefly, 100 ml of 1×PBS/0.05% sodium azide (pH 7.2) was used to pre-equilibrate the column before supernatant was sterile filtrated with a 0.22 µm vacuum filter (Corning) with 0.05% sodium azide was applied with a flow-rate of 1-2 ml/min. Then, 200 ml of 1×PBS/0.05% azide was applied to wash out unspecific binding. Bound HSA GST-fusions were eluted with 50 ml of 10 mM reduced glutathione (Sigma-Aldrich) diluted in 50 mM of Tris-HCl (pH 8.0). Eluted fractions were collected, upconcentrated and buffer-changed to 1×PBS/0.05% azide using Amicon Ultra-10 columns (Millipore). All fractions were stored in −20° C. with a concentration of 0.5-1 mg/ml. The column was washed and stored in 20% ethanol at 4° C.

Production of Human FcRn

Truncated monomeric His-tagged hFcRn was produced using a Baculovirus expression vector system, essentially as previously described (Kim et al., (1999) European journal of immunology 29, 2819-2825; Popov et al., (1996) Molecular immunology 33, 521-530). The receptors were purified using a HisTrap HP column supplied with $Ni^{2+}$ ions (GE Healthcare, UK). Prior to use, the column was pre-equilibrated with 1×PBS containing 0.05% sodium azide. The pH of the supernatant was adjusted with 1×PBS/0.05% sodium azide (pH 10.9) to pH 7.2, before applied to the HisTrap HP column with a flow rate of 5 ml $min^{-1}$. After washing with 200 ml of 1×PBS followed by 50 ml of 25 mM imidazole/1×PBS, bound receptor was eluted with 50 ml of 250 mM imidazole/1×PBS (pH 7.2-7.4). The protein was up-concentrated and buffer-changed to 1×PBS using Amicron Ultra-10 columns (Millipore) before applied on a HiLoad 26/600 Superdex 200 prep grade column (GE Healthcare) following the manufactures protocol. Eluted fractions were pooled and up-concentrated using Amicon Ultra columns (Millipore) and stored at 4° C.

Enzyme-Linked Immunosorbent Assay (ELISA)

Screening of GST-fused HSA variants were carried out by coating an anti-human IgG1 mutant variant (M252Y/S254T/T256E/H433K/N434F) with specificity for 4-hydroxy-3-iodo-5-nitrophenylacetic acid (10 μg/ml) in microtiter wells (Nunc). The plates were incubated over night at 4° C. before the wells were blocked with PBS/4% skimmed milk for 1 h at room temperature, followed by washing 4 times in PBS/T pH 6.0. A constant amount of His-tagged hFcRn (20 μg/ml) was diluted in PBS/T/4% skimmed milk pH 6.0, added to the wells, and incubated for 2 h at room temperature before wells were washed as above. Subsequently, 5 μg/ml of GST-tagged WT HSA and the mutant variants were diluted in PBS/T/4% skimmed milk pH 6.0 and added to the wells for 2 h at room temperature. After washing as above, a horseradish peroxidase-conjugated anti-GST antibody (GE Healthcare), diluted (1:3000) in PBS/T/4% skimmed milk pH 6.0, was then added and incubated for 1 h. After washing, bound HSA variants were detected using tetramethylbenzidine substrate (Calbiochem). The absorbance was measured at 620 nm using the Sunrise spectrophotometer (TECAN).

Surface Plasmon Resonance (SPR)

SPR experiments were performed on a BIAcore 3000 instrument (GE Healthcare) and amine coupling (GE Healthcare) was used for immobilization of GST-fused HSA variants on CM5 chips. 2 μg/ml of each was injected in 10 mM sodium acetate at pH 5.0 (GE Healthcare), essentially as described by the manufacturer. Unreacted moieties on the chip surfaces were blocked with 1 M ethanolamine. Experiments were done with phosphate buffers (67 mm phosphate buffer, 0.15 M NaCl, 0.005% Tween 20) at pH 6.0 or 7.4) for both running or dilution of samples. Kinetic measurements were performed by injecting serial dilutions of monomeric His-tagged hFcRn (1.0-0.015 μM) over immobilized HSA variants at pH 6.0, with a flow rate of 50 μl/min at 25° C. Kinetic rate values were calculated using the simple Langmuir 1:1 ligand binding model provided by the BIAevaluation 4.1 software. The closeness of the fit, described by the statistical value $\chi^2$, which represents the mean square, was lower than 5.0 in all affinity estimations. To correct for nonspecific binding and bulk buffer effects, binding responses obtained from the control CM5 surfaces and blank injections were subtracted from each interaction curve.

Coupling of HSA Variants to Carboxyl Coated Molday ION.

1.5 ml CL-30Q02-CA (5 mg Fe/ml) (BioPal) was buffer-changed to 50 mM MES (pH 5.5) with 100 MWCO spin columns (Millipore). Activation of the carboxyl groups was done by adding 600 μl and 900 μl of EDC and NHS solutions (GE healthcare), respectively, followed by 20 min incubation at RT on a rotating wheel. For the removal of unreacted reagents, the activated particles were passed over a NAP-G-25 column (GE healthcare) equilibrated with 50 mM MES buffer (pH 5.5) following the directions of the column manufacturer. 2 mg HSA variant (dissolved in 0.1 M sodium bicarbonate buffer (pH 8.0)) were used/ml CL-30Q02-CA and incubated 120 min on a rotating wheel at RT after mixing. Subsequently, the coupled particles were buffer-changed to 1×PBS/0.05% azid with 100 MWCO spin columns (Millipore) and stored at 4° C.

T84 Transcytosis Assay

The human epithelial cell line T84 (ATCC) was maintained in Dulbecco's modified Eagles Medium DMEM (Invitrogen) and HAM's F-12 medium (1:1) (Invitrogen), supplied with 10% heat inactivated FBS, 2 mM Lg and 50 U/ml PS (all from Bio-Wittaker). The cells were incubated at 37° C. in a humidified 5% $CO_2$, 95% air incubator. Transwell filters (1.12 $cm^2$) with PTFE membrane and 0.4 μm pore size (Corning Costar, Mass., USA) were incubated ON in growth medium before $1.0 \times 10^6$ cells/well were seeded. Transepithelial resistance (TER) where measured daily using a MILLICELL-ERS volt-ohm meter (MILLIPORE). The cells were cultured for 4-6 days before reaching a TER value of 1000-1500Ω×$cm^2$. Growth medium were exchanged daily.

Prior to experiments, the T84 monolayers were washed and incubated for 1 hour in Hank's HBSS buffer (Invitrogen). For measurement of apical to basolateral transport, 200 μl of normalized HSA variants (20-30 μg/ml) or HSA variants coupled to Molday IONs (100 μl/ml, pH 6.0 adjusted with 1 M MES) were added to the apical side followed by sampling of 400 μl of medium at 0 and 4 hours from the basolateral reservoirs with 500 μl HBSS buffer. In assays measuring transport in the opposite direction, 500 μl HSA (8 μg/ml) were added to the basolateral side followed by sampling of 150 μl of medium at 0 and 4 hours from the apical reservoirs with 200 μl HBSS buffer.

Transport of HSA variants and conjugates across the T84 cells was quantified using ELISA. HSA variants with known concentrations were used as standards. An anti-GST antibody (diluted 1:5000) from goat (GE healthcare) or an anti-HSA antibody (diluted 1:2000) from goat (Sigma) in 1×PBS were coated in 96-well NUNC plates and incubated at 4° C. overnight. Next, wells were blocked using 200 μl of 4% S/PBS for 1 hour before washed 4 times with PBS/T followed by adding of titrated amounts of harvested medium diluted in S/T/PBS. The plates were incubated for 1 hour at RT before washed as above. Subsequently, an HRP-conjugated anti-HSA antibody from mouse (Abcam), diluted 1:5000 in S/T/PBS, was added and incubated for 1 hour at RT. The plates were washed as above before 100 μl of the 3,3',5,5'-Tetramethylbenzidine solution (Merck) was added. Absorbance was measured at 620 nm using the Sunrise spectrophotometer (TECAN).

RESULTS

To compare the binding capacities of the HSA fusions at neutral pH, normalized HSA-GST variants were added to hFcRn captured on a human IgG mutant, and bound HSA-GST variants were detected using an HRP-conjugated anti-GST antibody from goat (FIG. 11F), which showed that none of the mutant variants bound the receptor at neutral pH (FIG. 11).

To compare the binding capacities of the HSA fusions at acidic pH, titrated amounts of normalized HSA-GST variants were added to hFcRn captured on a human IgG mutant, and bound HSA-GST variants were detected using an HRP-conjugated anti-GST antibody from goat. KP and VA bound equally well and considerably better than the WT while the combination of KP/VA gave further improvement whereas KP/EQ/TM/VA bound strongest of all mutants at pH 6.0. At neutral pH, none of the mutant variants showed detectable binding except for KP/EQ/TM/VA, which bound strongly.

Figure 13:
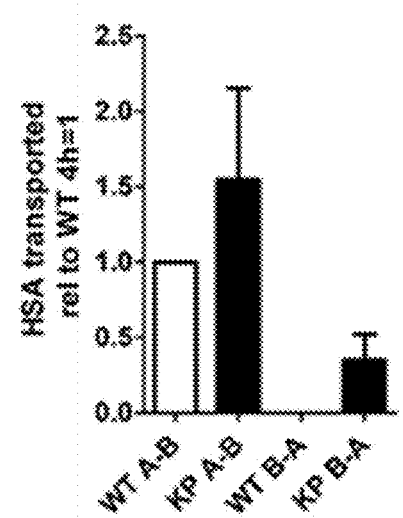
Figure 15:
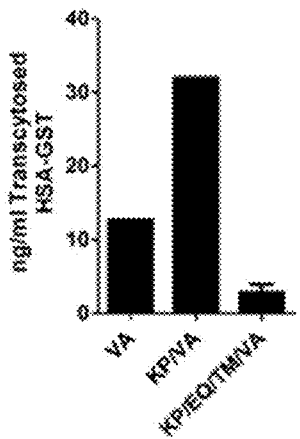
FIG. 15 shows transcytosis of HSA-GST variants across polarized human cells. ELISA quantification of the amounts of HSA VA, KP/VA and KP/EQ/TM/VA GST fusions transported from the apical to the basolateral side of polarized T84 cells grown in a Transwell system.

To investigate whether HSA could be transported in an FcRn-dependent fashion across an epithelial layer that express endogenous hFcRn, a Transwell system was used to measure FcRn-mediated IgG transport. First, transport of unfused WT HSA and KP was measured in both directions. Efficient transport was only measured from apical to basolateral direction where more of the KP was shown to be transported than the WT (FIG. 15). In the basolateral to the apical direction only minor amounts of the KP variants was shown to be transported while no WT was detected (FIG. 13).

Figure 14:
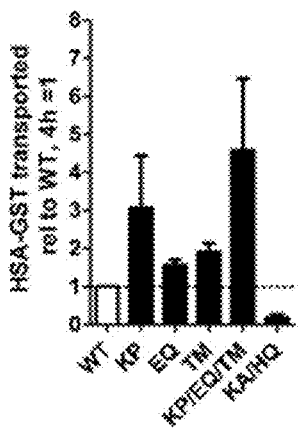
Figure 16A:
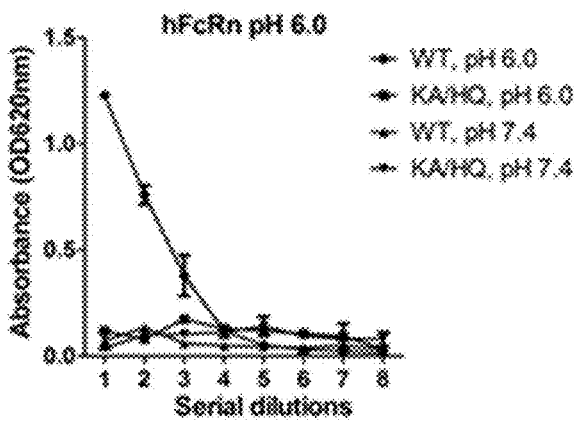
FIG. 16A and FIG. 16B shows transcytosis of HSA coupled NPs across polarized human cells. (A) ELISA showing binding at pH 6.0 and 7.4 of NPs coupled with WT HSA or KA/HQ.
Figure 16B:
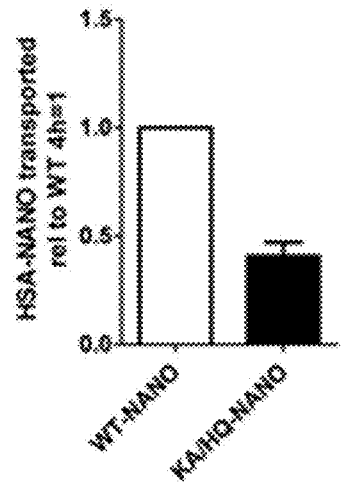

Furthermore, WT HSA-GST was compared with KA/HQ-GST, and equal amounts of these were added to the apical reservoirs of the Transwell system. Samples were collected from the basolateral reservoir at time points 0 and 4 hours post addition to the apical side. Transported HSA fusions were quantified using the ELISA where the fusions are captured on an anti-GST antibody and bound fusions are detected using an HRP-conjugated anti-HSA antibody. A striking difference in transport efficacy was detected, as 5-fold more of the WT fusion was transported than the double mutant (KA/HQ) lacking binding to hFcRn (FIG. 14). Thus, these data strongly support that FcRn expressed in human epithelium is capable of transcytose HSA across the cellular layer. It was then assessed whether or not a HSA variant with improved binding to hFcRn (KP) was transcytosed more efficiently than the WT counterpart (FIG. 14). It was found that introduction of the single KP mutation increased the transport efficacy by almost 3-fold compared with the WT (FIG. 16). The single mutants EQ and TM were transported more efficient than the WT far from that of KP, while the combination of KP/TM/EQ resulted in approximately 2-fold enhanced transport compared with KP (FIG. 14).

Next, transcytosis from the apical to basolateral side of VA was compared with that of KP/VA and KP/TM/EQ/VA and found that KP/VA was transported 3-fold more efficient than VA (FIG. 15), while KP/TM/EQ/VA, which binds strongly at both pH conditions, was not transported (FIG. 15).

It was next addressed whether NPs conjugated to HSA could be shuttled across the polarized cellular layer. WT HSA and KA/HQ were site-specific conjugated to the NPs via the free cysteine residue within DI, distal from the binding site for FcRn. The NPs were added to the apical side and the amounts transported across the cells and released at the basolateral was quantified and showed that 2-fold more NPs conjugated to WT HSA was transported than KA/HQ (FIG. 16).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A variant human serum albumin (HSA) fragment that binds to FcRn, wherein the variant FcRn binding fragment comprises a glutamine residue in position 505, a methionine residue in position 527 and a proline residue in position 573.

2. The variant HSA fragment according to claim 1, wherein the variant HSA fragment has increased binding to FcRn at pH 6.0 relative to the corresponding wild type HSA fragment.

3. The variant HSA fragment according to claim 1, wherein the HSA fragment is the DIII domain of HSA.

4. A nucleic acid encoding the variant HSA fragment thereof according to claim 1.

5. A pharmaceutical composition comprising the variant HSA fragment according to claim 1.

6. A fusion protein comprising the variant HSA fragment according to claim 1.

7. A nucleic acid encoding the fusion protein according to claim 6.

8. A pharmaceutical composition comprising the fusion protein according to claim 6.

* * * * *

```
                        SEQUENCE LISTING

<160> NUMBER OF SEQ ID NOS: 1

<210> SEQ ID NO 1
<211> LENGTH: 585
<212> TYPE: PRT
<213> ORGANISM: Artificial sequence
<220> FEATURE:
<223> OTHER INFORMATION: Synthetic

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110
```

```
Pro Arg Leu Val Arg Pro Glu Val Asp Val Met Cys Thr Ala Phe His
            115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
```

-continued

```
            530                 535                 540
Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```